US011243190B2

(12) United States Patent
Bai et al.

(10) Patent No.: US 11,243,190 B2
(45) **Date of Patent: *Feb. 8, 2022**

(54) QUANTITATIVE LIQUID TEXTURE MEASUREMENT METHOD

(71) Applicant: Frito-Lay North America, Inc., Plano, TX (US)

(72) Inventors: Ou Bai, Plano, TX (US); Wilfred Marcellien Bourg, Jr., Melissa, TX (US); Scott Fagan, Dallas, TX (US); Enrique Michel-Sanchez, Dallas, TX (US); Shahmeer Ali Mirza, Dallas, TX (US); Scott G. Richardson, Gainesville, TX (US); Chen C. Shao, Plano, TX (US)

(73) Assignee: Frito-Lay North America, Inc., Plano, TX (US)

( * ) Notice: Subject to any disclaimer, the term of this patent is extended or adjusted under 35 U.S.C. 154(b) by 122 days.

This patent is subject to a terminal disclaimer.

(21) Appl. No.: 16/704,560

(22) Filed: Dec. 5, 2019

(65) Prior Publication Data

US 2020/0110058 A1 Apr. 9, 2020

Related U.S. Application Data

(60) Continuation of application No. 16/132,830, filed on Sep. 17, 2018, now Pat. No. 10,605,787, which is a (Continued)

(51) Int. Cl.
*G01N 29/14* (2006.01)
*G01N 29/24* (2006.01)
(Continued)

(52) U.S. Cl.
CPC ......... *G01N 29/2418* (2013.01); *G01N 29/02* (2013.01); *G01N 29/036* (2013.01);
(Continued)

(58) Field of Classification Search
CPC ...................................................... G01N 33/02
See application file for complete search history.

(56) References Cited

U.S. PATENT DOCUMENTS 4,051,372 A 9/1977 Aine
4,169,662 A 10/1979 Kaule et al.
(Continued)

FOREIGN PATENT DOCUMENTS

DE 329319 11/1920
DE 3939411 6/1991
(Continued)

OTHER PUBLICATIONS

Lee et al., "Evaluation of the firmness measurement of fruit by using a non-contact ultrasonic technique," Industrial Electronics and Applications (ICIEA), 2013 8th IEEE Conference ON, IEEE, Jun. 19, 2013, pp. 1331-1336.

(Continued)

*Primary Examiner* — Lisa M Caputo
*Assistant Examiner* — Alex T Devito
(74) *Attorney, Agent, or Firm* — Barnes & Thornburg LLP; G. Peter Nichols

(57) ABSTRACT

A photo acoustic non-destructive measurement apparatus and method for quantitatively measuring texture of a liquid. The apparatus includes a laser generating tool, an acoustic capturing device, and a data processing unit. The laser generating tool directs a laser towards a surface of a liquid contained in a container and creates pressure waves that propagate through the air and produce an acoustic signal. The acoustic capturing device records and forwards the signal to a data processing unit. The data processing unit further comprises a digital signal processing module that processes the received acoustic signal. A statistical processing module further filters the acoustic signal from the data (Continued)

processing unit and generates a quantitative acoustic model for texture attributes such as hardness and fracturability. The quantitative model is correlated with a qualitative texture measurement from a descriptive expert panel. Textures of liquids are quantitatively measured with the quantitative acoustic model.

8 Claims, 24 Drawing Sheets

Related U.S. Application Data division of application No. 15/459,828, filed on Mar. 15, 2017, now Pat. No. 10,107,785, which is a continuation-in-part of application No. 15/380,943, filed on Dec. 15, 2016, now Pat. No. 10,101,143, which is a continuation-in-part of application No. 15/380,622, filed on Dec. 15, 2016, now Pat. No. 10,048,232, which is a continuation of application No. 14/864,593, filed on Sep. 24, 2015, now Pat. No. 9,541,537, which is a continuation of application No. 14/864,593, filed on Sep. 24, 2015, now Pat. No. 9,541,537.

(51) Int. Cl.
*G01N 29/02* (2006.01)
*G01N 33/14* (2006.01)
*G01N 29/036* (2006.01)
*G01N 33/10* (2006.01)
*G01H 9/00* (2006.01)

(52) U.S. Cl.
CPC ............ *G01N 33/10* (2013.01); *G01N 33/14* (2013.01); *G01H 9/008* (2013.01); *G01N 2291/022* (2013.01); *G01N 2291/02818* (2013.01); *G01N 2291/02827* (2013.01)

(56) References Cited

U.S. PATENT DOCUMENTS

| | | | |
|---|---|---|---|
| 4,184,768 | A | 1/1980 | Murphy |
| 4,187,026 | A | 2/1980 | Schaffer |
| 4,234,258 | A | 11/1980 | Frosch |
| 4,236,827 | A | 12/1980 | Horiba |
| 4,325,252 | A | 4/1982 | Miller |
| 4,381,148 | A | 4/1983 | Ulrich et al. |
| 4,479,265 | A | 10/1984 | Muscatell |
| 4,562,736 | A | 1/1986 | Iwasaki |
| 4,866,283 | A | 9/1989 | Hill |
| 4,899,589 | A | 2/1990 | Thompson |
| 5,048,340 | A | 9/1991 | Thompson |
| 5,070,733 | A | 12/1991 | Nagata |
| 5,121,426 | A | 6/1992 | Baumhauer |
| 5,151,590 | A | 9/1992 | Takamoto et al. |
| 5,152,401 | A | 10/1992 | Affeldt |
| 5,161,408 | A | 11/1992 | McRae |
| 5,226,076 | A | 7/1993 | Baumhauer |
| 5,251,486 | A | 10/1993 | Thompson |
| 5,286,313 | A | 2/1994 | Schultz |
| 5,372,030 | A | 12/1994 | Prussia |
| 5,526,689 | A | 6/1996 | Coulter |
| 5,588,428 | A | 12/1996 | Smith |
| 5,691,473 | A | 11/1997 | Peleg |
| 5,751,416 | A | 5/1998 | Singh |
| 5,780,724 | A | 7/1998 | Olender |
| 5,804,727 | A | 9/1998 | Lu |
| 5,825,898 | A | 10/1998 | Marash |
| 5,827,974 | A | 10/1998 | Nussinovitch |
| 5,847,825 | A | 12/1998 | Alexander |
| 5,848,172 | A | 12/1998 | Allen |
| 5,922,387 | A | 7/1999 | Parada |
| 6,034,768 | A | 3/2000 | Fraser |
| 6,057,927 | A | 5/2000 | Levesque et al. |
| 6,122,389 | A | 9/2000 | Grosz |
| 6,256,100 | B1 | 7/2001 | Banet |
| 6,276,536 | B1 | 8/2001 | Terasaki et al. |
| 6,311,558 | B1 | 11/2001 | Clark |
| 6,385,558 | B1 | 5/2002 | Schlemm |
| 6,407,811 | B1 | 6/2002 | Snyder |
| 6,466,309 | B1 | 10/2002 | Kossakovski |
| 6,494,098 | B1 | 12/2002 | Leybovich |
| 6,531,707 | B1 | 3/2003 | Favreau |
| 6,532,821 | B2 | 3/2003 | Lamouche |
| 6,539,781 | B1 | 4/2003 | Crezee |
| 6,628,404 | B1 | 9/2003 | Kelley |
| 6,657,721 | B1 | 12/2003 | Palleschi |
| 6,694,173 | B1 | 2/2004 | Bende |
| 6,753,957 | B1 | 6/2004 | Graft |
| 6,771,368 | B1 | 8/2004 | Chadwick |
| 6,792,324 | B2 | 9/2004 | Trinkel |
| 6,823,736 | B1 | 11/2004 | Brock |
| 6,857,317 | B2 | 2/2005 | Sakurai |
| 6,909,505 | B2 | 6/2005 | Lucas |
| 6,944,204 | B2 | 9/2005 | Zhou |
| 6,987,564 | B2 | 1/2006 | Gornushkin |
| 7,092,807 | B2 | 8/2006 | Kumar |
| 7,117,034 | B2 | 10/2006 | Kronberg |
| 7,165,451 | B1 | 1/2007 | Brooks |
| 7,195,731 | B2 | 3/2007 | Jones |
| 7,595,463 | B2 | 9/2009 | Weick |
| 7,692,788 | B2 | 4/2010 | Popp |
| 7,802,477 | B2 | 9/2010 | Sakurai |
| 7,860,277 | B2 | 12/2010 | Mulder |
| 8,319,964 | B2 | 11/2012 | Halm |
| 8,368,289 | B2 | 2/2013 | Karabutov |
| 8,567,250 | B2 | 10/2013 | Loeser |
| 8,619,255 | B2 | 12/2013 | Gennadievich |
| 8,659,753 | B1 | 2/2014 | Cabaio |
| 8,638,956 | B2 | 4/2014 | Deng |
| 8,891,073 | B2 | 11/2014 | Effenberger, Jr |
| 9,032,798 | B2 | 5/2015 | Sakakibara |
| 9,068,926 | B2 | 6/2015 | Schade |
| 9,159,126 | B2 | 10/2015 | Johnson |
| 9,285,310 | B2 | 3/2016 | Patel |
| 9,358,636 | B2 | 6/2016 | Hammann |
| 9,541,537 | B1 | 1/2017 | Bai |
| 2002/0039186 | A1 | 4/2002 | Rosenberg |
| 2002/0144458 | A1 | 10/2002 | Hunter |
| 2003/0095266 | A1 | 5/2003 | Detalle |
| 2003/0216875 | A1 | 11/2003 | Sakurai |
| 2004/0197012 | A1 | 10/2004 | Bourg, Jr. et al. |
| 2007/0218556 | A1 | 9/2007 | Harris |
| 2007/0229834 | A1 | 10/2007 | Patel |
| 2008/0003339 | A1 | 1/2008 | Johnson |
| 2008/0093775 | A1 | 4/2008 | Menoni |
| 2008/0124433 | A1 | 5/2008 | Yelden |
| 2008/0204757 | A1 | 8/2008 | Manning |
| 2008/0253648 | A1 | 10/2008 | Mulder |
| 2009/0316927 | A1 | 12/2009 | Ferrill |
| 2010/0070197 | A1 | 3/2010 | Wang |
| 2010/0297671 | A1 | 11/2010 | Tschmelak |
| 2011/0033062 | A1 | 2/2011 | Deng |
| 2011/0088477 | A1 | 4/2011 | Someda |
| 2011/0294987 | A1 | 12/2011 | Kanazaki |
| 2012/0002193 | A1 | 1/2012 | Elliott |
| 2012/0008802 | A1 | 1/2012 | Felber |
| 2012/0014534 | A1 | 1/2012 | Bodley |
| 2012/0020485 | A1 | 1/2012 | Visser |
| 2012/0099732 | A1 | 4/2012 | Visser |
| 2012/0202277 | A1 | 8/2012 | Wagner |
| 2012/0206722 | A1 | 8/2012 | Grigoropoulos |
| 2012/0234102 | A1 | 8/2012 | Johnson |
| 2012/0314214 | A1 | 12/2012 | Alexander |
| 2013/0058514 | A1 | 3/2013 | Akino |
| 2013/0118227 | A1 | 5/2013 | Sakaibara |
| 2013/0150114 | A1 | 6/2013 | Bodley |
| 2013/0201316 | A1 | 8/2013 | Binder |
| 2013/0228016 | A1 | 9/2013 | Sakurai |
| 2013/0266925 | A1 | 10/2013 | Nunamaker |
| 2013/0344208 | A1 | 12/2013 | Singh |
| 2014/0011690 | A1 | 1/2014 | Dimov |

(56) References Cited

U.S. PATENT DOCUMENTS

| | | | |
|---|---|---|---|
| 2014/0003819 | A1 | 2/2014 | Loeser |
| 2014/0033819 | A1 | 2/2014 | Loeser et al. |
| 2014/0079248 | A1 | 3/2014 | Short |
| 2014/0125965 | A1 | 5/2014 | Nagli |
| 2015/0204822 | A1 | 7/2015 | Horan |
| 2017/0027168 | A1 | 2/2017 | Heath |
| 2017/0086479 | A1 | 3/2017 | Bai |
| 2017/0089869 | A1 | 3/2017 | Bai |
| 2017/0097222 | A1 | 4/2017 | Bai |
| 2017/0097324 | A1 | 4/2017 | Bai |
| 2017/0176309 | A1 | 6/2017 | Bai |
| 2018/0011069 | A1 | 1/2018 | Bai |

FOREIGN PATENT DOCUMENTS

| | | |
|---|---|---|
| DE | 19632867 | 2/1998 |
| DE | 19716672 | 6/1998 |
| DE | 69320728 | 1/1999 |
| DE | 10315541 | 10/2001 |
| DE | 102005051643 | 4/2006 |
| DE | 102006035730 | 1/2008 |
| EP | 1348955 | 10/2003 |
| ES | 2147141 | 8/2000 |
| JP | 2004085303 | 3/2004 |
| JP | 2006227021 | 8/2006 |
| JP | 2009008696 | 1/2009 |
| UA | 104233 | 1/2014 |
| WO | WO 9425851 | 11/1994 |
| WO | WO 9857145 | 12/1998 |
| WO | WO 9915890 | 4/1999 |
| WO | WO 02057774 | 7/2002 |
| WO | WO 02079765 | 10/2002 |
| WO | WO 2009047549 | 4/2009 |
| WO | WO 2013004210 | 1/2013 |
| WO | WO 2013027445 | 2/2013 |
| WO | WO 2014180568 | 11/2014 |

OTHER PUBLICATIONS

Examination Report dated Aug. 10, 2020 in European Application No. 16849783.2.

Srisawas et al., "Acoustic Testing of Snack Food Crispness Using Neural Networks," Food Engineering and Bioprocess Technology School of Environment, Resources and Development, Journal of Texture Studies 34, Jul. 30, 2003, pp. 401-420.

Chauvin et al., Standard Scales for Crispness, Crackliness and Crunchiness in Dry and Wet Foods: Relationship with Acoustical Determinations, Journal of Texture Studies, vol. 39, No. 4, Aug. 1, 2008, pp. 345-368.

De Belie et al., "Crispness Judgement of Royal Gala Apples Based on Chewing Sounds," Biosystems Engineering, Academic Press,UK, vol. 81, No. 3, Mar. 1, 2002, pp. 297-303.

Duizer et al., "A review of acoustic research for studying the sensory perception of crisp, crunchy and crackly textures," Trends in Food Science and Technology, Elsevier Science Publishers, GB, vol. 12, No. 1, Jan. 1, 2001, pp. 17-24.

Roudaut et al., "Crispness: a critical review on sensory and material science approaches," Trends in Food Science and Technology, Elsevier Science Publishers, GB, vol. 13, No. 6-7, Jun. 1, 2002, pp. 217-227.

European Patent Office, "Supplemental European Search Report" for related EP Application No. 17760967.4, Sep. 2019, 13 pages.

Patent Cooperation Treaty, "International Preliminary Report on Patentability," for related PCT Application No. PCT/US2018/051779, dated Oct. 11, 2019, 30 pages.

Aguilera, Jose Miguel, "Why food microstructure?" J. Food Engineering 67 (2005) 3-11 (9 pages).

Chauvin, Maite A., et al., "Relationship Between Instrumental and Sensory Determination of Apple and Pear Texture," J. Food Quality, 33 (2010) 181-198 (18 pages).

Mohamed, Abdellatif et al., "Estimation of HRW wheat heat damage by DSC, capillary zone electrophoresis, photoacoustic spectroscopy and rheometry" Science Direct (19 pages).

Khairi, MOhd, "Contact and non-contact ultrasonic measurement in the food industry: a review," Measurement Science and Technology, vol. 27, No. 1, Dec. 1, 2015, abstract, 24 pages.

Abdel-Salam et al., "Qualitative evaluation of maternal milk and commercial infant formulas via LIBS" Talanta 115 (2013) 422-426 (5 pages).

Applied Spectra, Inc.—Technique—Gate Delay, http://www.apliedspectra.com/technology/gate-delay.html printed Sep. 29. 2014 (6 pages).

Assion et al., "Fermtosecond laser-induced-breakdown spectrometry for Ca2+ analysis of biological samples with high spatial resolution," Appl Phys. 2003, 77:391-97.

Kongbonga et al., Classification of vegetable oils based on their concentration of saturated fatty acids using laser induced breakdown spectroscopy (LIBS, Food Chemistry 147 (2014) 327-331 (5 pages).

Berer et al., "Remote photoacoustic imaging for material inspection" 2$^{nd}$ International Symposium on Laser-Ultrasonics—Science, Technology and Applications, Journal of Physics: Conference Series 278 (2011) 012034 (4 pages).

Kowalczyk et al., "Bulk measurement of copper and sodium content in Culn0.7Ga0.3Se2 (CIGS) solar cells with nanosecond pulse length laser induce breakdown spectroscopy (LIBS)" Department of Physics and Astronomy, University of Hawaii, Jan. 8, 2013 (6 pages).

Lanza et al., "Calibrating the ChemCM laser-induced breakdown spectroscopy instrument for carbonate minerals on Mars" May 1, 2010, vol. 49, No. 13, Applied Optics (7 pages).

Lei et al., "Time-resolved characterization of laser-induced plasma from fresh potatoes" Spectrochimica Acta Part B 64 (2009) 891-898 (8 pages).

Menut et al., "Micor-laser-induced breakdown spectroscopy technique: a powerful method for performing quantitative surface mapping on conductive and nonconductive samples," Oct. 2003, Applied Optics, vol. 42, No. 3 0, pp. 6063-6071.

"NRC-CNRC" "Laser-Induced Breakdown Spectroscopy (LIBS) Optical Sensing Technology for Rapid On-site Chemical Analysis" (4 pages).

PCT International Search Report and Written Opinion for PCT/US2015/052510 dated Dec. 14, 2015 (9 pages).

Pedarnig, "Application of laser-induced breakdown spectroscopy to the analysis of secondary materials in industrial production" 2014 Woodhead Publishing Limited (26 pages).

Ravishankar et al., "Photo-acoustic emission measurements in liquid-based food and aqueous products," 2007, 12 pages.

Samek et al., "Ultra-short laser puls ablation using shear-force feedback: Femtosecond laser induced breakdown spectroscopy feasibility study," Spectrochimica Acta Part B, pp. 1225-1229.

Slaughter, "Nondestrructive Quality of Measurement of Horticultural Crops," University of CA, Davis, 2011, 13 pages.

Sun et al., "Correction of self-absorption effect in calibration-free laser-induced breakdown spectroscopy by an internal reference method" Talanta 79 (2009) 388-395 (8 pages).

"TSI Laser Induced Breakdown Spectroscopy, Chemreveal LIBS Desktop Elemental Analyzer," from http://www.tsi.com/ChemReveai-LIBS-Desktop-Analyzer/, printed Aug. 6, 2014 (3 pages).

"What is LIBS from http://www.spectrolabsystes.net/products/analytical-instruments/laser-induced-beakdown . . . . " printed Aug. 6, 2014 (1 page).

Cravetchi et al., "Scanning microanalysis of A1 alloys by laser-induced breakdown spectroscopy" Spectrochimica Acta Part B 59 (2004) 1439-1450 (12 pages).

Kossakovski et al., "Topographical and Chemical Microanalysis of Surfaces with a Scanning Probe Microscope and Laser-Induced Breakdown Spectroscopy" Anal. Chem. 2000, 72, 4731-4737 (7 pages).

Office Action dated Jun. 23, 2020 in U.S. Appl. No. 16/044,565.

Extended Search Report dated Apr. 8, 2021 in European Application No. 18858520.2.

1700

1701 1702

1711

1712

| FOOD PRODUCT | FOOD COMPOSITE NUMBER RANGE |
| --- | --- |
| SOLID A | 5.3 - 6.3 |
| SOLID B | 7.2 - 7.6 |
| * | |
| * | |
| * | |
| * | |
| SOLID C | 9.3 - 10.3 |
| SOLID D | 14.2 - 14.6 |
| * | |
| * | |
| * | |
| * | |

FIG. 17

QUANTITATIVE LIQUID TEXTURE MEASUREMENT METHOD

CROSS-REFERENCE TO RELATED APPLICATIONS

This application is a continuation (CON) of U.S. application Ser. No. 16/132,830 filed Sep. 17, 2018, published Jan. 17, 2019, as US Publication No. 2019-0017972, which is a divisional (DIV) application of U.S. application Ser. No. 15/459,828 filed Mar. 15, 2017, published Jun. 29, 2017, as US Publication No. 2017-0184551, which in turn was a continuation-in-part (CIP) of U.S. application Ser. No. 15/380,622 filed Dec. 15, 2016, published Apr. 6, 2017, as US Publication No. 2017-0097324, and U.S. application Ser. No. 15/380,943 filed Dec. 15, 2016, published Apr. 6, 2017, as US Publication No. 2017-0097222, which are both continuation (CON) applications of U.S. application Ser. No. 14/864,593 filed Sep. 24, 2015, now U.S. Pat. No. 9,541,537 issued Jan. 10, 2017. All the applications, publications and patents listed in this paragraph are incorporated herein by reference in their entirety as examples.

FIELD OF THE INVENTION

The present invention relates to a quantitative measurement of texture for liquids using non-invasive photo acoustic techniques.

PRIOR ART AND BACKGROUND OF THE INVENTION

Prior Art Background

Texture is one of the most important sensory characteristics that determine consumer preference for food products and is usually assessed by sensory evaluation. However, sensory evaluation is time-consuming and expensive, and therefore, reliable and practical instrumental methods are needed to accurately predict sensory texture attributes and other food snack properties.

When a food snack such as potato chip is manufactured, textural properties are dependent on raw material characteristics (i.e. low solids or high solids potatoes) and the processing conditions that the raw material undergoes such as temperature profile, slice thickness, as well as finished product characteristics such as moisture, oil content, etc.

The crispiness, softness and/or crunchiness of a potato chip are just a few examples of texture and mouthfeel characteristics that make food appealing and satisfying to consumers. Texture is one of the major criteria which consumers use to judge the quality and freshness of many foods. When a food produces a physical sensation in the mouth (hard, soft, crisp, moist, dry), the consumer has a basis for determining the food's quality (fresh, stale, tender, ripe)

A major challenge is how to accurately and objectively measure texture and mouthfeel for liquids and solids. Texture is a composite property related to a number of physical properties (e.g., hardness and fracturability), and the relationship is complex. Texture or mouthfeel cannot be quantitatively measured in a single value obtained from an instrument. Mouthfeel is hard to define as it involves food's entire physical and chemical interaction in the mouth—from initial perception on the palate, to first bite, through mastication and finally, the act of swallowing. There is a need to quantitatively measure the food interaction in the mouth.

A problem with hardness is that their correlations with sensory tests are not always as high as expected. In many instances, the metric of peak force exerted on a potato chip does not adequately replicate the texture experienced by consumers. Therefore, consumers' judgments of hardness can be more nuanced than a simple peak force metric from a destructive analytical test.

Presently, there is no good correlation of any type between instrument readings and taste panel scores. The issue is that no instrument is capable of manipulating a food product precisely the same way as the human mouth during mastication. For example, an instrument may compress a food product between two plates, while a human would be biting down with incisors. Therefore, there is a need for a quantitative texture measurement that has a good correlation with a qualitative measurement from an expert panel.

Complexity in tasting wine can mean many things. The ability to detect and appreciate complexity in wine will become a good gauge of the overall progress in learning how to taste wine. However, there are currently no quantitative methods to measure the complex flavors in a wine. Typically, a sip of wine into taken into a mouth and sucking on it as if pulling it through a straw simply aerates the wine and circulates it throughout your mouth. There is no single formula for all wines, but there should always be balance between the flavors. If a wine is too sour, too sugary, too astringent, too hot (alcoholic), too bitter, or too flabby (lack of acid) then it is not a well-balanced wine. Aside from simply identifying flavors such as fruit, flower, herb, mineral, barrel, taste buds are used to determine if a wine is balanced, harmonious, complex, evolved, and complete. A balanced wine should have its basic flavor components in good proportion. The taste buds detect sweet, sour, salty, and bitter. Sweet (residual sugar) and sour (acidity) are obviously important components of wine. However, there are currently no quantitative methods to measure the balance and other components in a wine.

Similar to wine tasting, current coffee tasting methods do not provide a quantitative method to measure coffee flavors and taste. Currently in the food industry mouthfeel of beverages are characterized by qualitative rheological means. For beverages sometimes a rheometer is utilized to measure the viscosity or elasticity of fluid. While the measurement have been of vital importance to the industry, they do not explain rheology the consumer experiences when the sample comes into contact with human saliva. Saliva is a watery substance located in the mouths of humans and animals, secreted by the salivary glands. Human saliva is 99.5% water, while the other 0.5% consists of electrolytes, mucus, glycoproteins, enzymes, antibacterial, and bacteria compounds such as secretory IgA and lysozyme. The enzymes found in saliva are essential in beginning the process of digestion of dietary starches and fats. Furthermore, saliva serves a lubricative function, wetting food and permitting the initiation of swallowing, and protecting the mucosal surfaces of the oral cavity from desiccation. While the characteristic of saliva such as pH, viscosity and others are different from individual to individual, there are means to calibrate the measurement with beverage standards. More specifically, current qualitative and quantitative measurements of beverage texture exhibit measurement errors that would require large sample sizes to achieve statistical significance. As an example, differentiating sweeteners at the concentrations they are found in beverages in a rheological manner can prove to be very difficult; in other words to distinguish the viscosity of a Diet Pepsi® vs. a regular Pepsi® is difficult given the measurement error; however, when in contact with saliva, different sweeteners can have different interactions with human saliva given their chemical composition, the mixture of the beverage and the saliva produces viscosity differences that cannot be differentiated by current measurement methods.

Prior Art Texture Measurement System

The Universal TA-XT2 Texture Analyzer from Texture Technologies Corp., can perform a complete TPA calculation and comes with multiple standard probes, including various sizes of needles, cones, cylinders, punches, knives and balls. FIG. 1. Illustrates a prior art system for measuring texture attributes such as hardness and fracturability with a TA-XT2 Texture Analyzer. The system includes a probe (0101) that exerts a force on a food snack such as a potato chip and measure the amount of force required to break the chip. Hardness may be measured as a force required to deform the product to given distance, i.e., force to compress between molars, bite through with incisors, compress between tongue and palate.

Prior Art Texture Measurement Method

As generally shown in FIG. 2, a prior art texture measurement method associated with the prior art system may include the steps comprising:

(1) placing a food snack on a surface (0201);

(2) with a probe, exerting a force and break/deform the food snack (0202);

(3) generating an acoustic signal from the food snack or measuring the force exerted (0203);

Force exerted may depend on the shape of the food snack. For example, a U shaped food snack or a curvy shaped food snack may be placed in either direction and the force exerted to break the food snack may be different. Therefore, there is a need for a shape independent quantitative texture measurement.

(4) capturing the acoustic signal with an acoustic capturing device or record the force required to break the food snack (0204);

acoustic signal is captured for a period of time at preset frequencies and the signal is plotted as Time (seconds) vs. Intensity (dB). There is a need to measure acoustic signal in a wide range of frequencies.

(5) generating a texture model from the acoustic signal (0205); and

A model for texture attributes such as hardness and fracturability is developed from the Time vs. Intensity plot for the food snack. Alternatively, a model from measured force may also be used to develop a model.

(6) measuring the texture attribute of the food snack from the texture model.

Texture attributes of a food snack is measured from the model developed in step (0205). The texture attributes are correlated to a qualitative texture attributes number from an expert panel as described below in FIG. 3.

Prior Art Texture Correlation Method

As generally shown in FIG. 3, a prior art texture correlation method may include the steps comprising:

(1) shipping food snack samples to an expert panel (0301);

The shipping of the food snack samples may take time and the food snack may undergo texture change during the shipping process. Therefore, there is a need to limit the number of times food snacks are shipped the expert panel.

(2) Qualitatively analyzing the food snack samples (0302);

The process starts with a well-trained sensory panel to carry out a meaningful texture profile analysis, a panel of judges needs to have prior rating knowledge of the texture classification system, the use of standard rating scales and the correct procedures related to the mechanics of testing. Panelist training starts with a clear definition of each attribute. Furthermore, the techniques used to evaluate the food product should be explicitly specified, explaining how the food product is placed in the mouth, whether it is acted upon by the teeth (and which teeth) or by the tongue and what particular sensation is to be evaluated. Panelists are given reference standards for evaluation so they can practice their sensory evaluation techniques and the use of scales. Hardness and fracturability are usually considered to be the most important texture attribute. Presently there is no good correlation of any type between instrument readings and taste panel scores. Presently there are no instruments capable of manipulating a food product precisely the same way as the human mouth during mastication. For example, an instrument may compress a food product between two plates, while a human would be biting down with incisors. In fact, what an instrument measures may not relate at all to what the consumer perceives. Therefore, there is a need to have a system that can quantitatively measure texture attributes and correlate to the taste panel scores.

(3) assigning a descriptive panel number for the texture attributes of the food snack sample (0303);

An organoleptic sensory evaluation is performed in which the trained panelists assign intensity levels on various descriptors/texture attributes. For example, for evaluating the potato chips, hardness may be considered one important attribute. In this case, panelists assign a hardness score based on a scale, where 1 equals extremely soft and 15 equals extremely hard. The panelists may rate the hardness of potato chip samples A, B and C's. After taste paneling is complete, instrument readings of the food product are made as described below in step (0304).

(4) Measure texture attributes using an invasive analytical method (0304);

There is a need that the instrumental technique selected duplicates as closely as possible how the mouth manipulates the particular food product. The instrument should apply the same amount of force in the same direction and at the same rate as the mouth and teeth do during mastication. The instrument may record acoustic signals for a period of time and generate a model. Therefore, there is a need for recording sound in a wider frequency range.

(5) Correlate the analytical and the qualitative texture attributes (0305); and Statistically correlate between sensory data (descriptive panel number) and instrumental measurements. Currently, correlation based on Intensity vs. Time measurements, generate a weak correlation statistically.

Therefore, there is a need for a strong correlation between descriptive panel number and the analytical model.

(6) Generating a correlation model (0306).

Consequently, there is a need for a non-invasive quantitative texture measurement that accomplishes the following objectives:

Provide a quantitative method to measure finished product attributes such as viscosity, density, mouthfeel, astringency, mouth coating, sweetness, sensory, and rheology.

Provide for quantitative analytical measurement of the textural attributes such as hardness, fracturability, crispiness, and surface oiliness.

Provide for analyzing frequency domain data to accurately model the texture attributes.

Provide for acoustic signal capture in a broad frequency range from 0 to 5000 KHz Provide for shape independent quantitative test for texture measurement.

Provide for a non-invasive quantitative measurement of texture of a liquid.

Provide for quantitative measurement of texture with minimum samples with greater accuracy and reliability.

Provide for a less expensive quantitative texture measurement test.

Provide for instant results of the quantitative measurement.

Provide for an accurate model with good correlation with an $R^2$ greater than 0.9.

Provide for high resolution texture measurement with better than 5% accuracy.

Provide for repeatable and reproducible quantitative measurements of liquids.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention in various embodiments addresses one or more of the above objectives in the following manner. The texture measuring apparatus includes an energy excitation tool, an acoustic capturing device, and a data processing unit. The energy excitation tool directs a laser towards a liquid placed on a surface and creates rapid expansion of the material which in results in creation of air pressure waves that propagate through the air and produce an acoustic signal. The acoustic capturing device records and forwards the signal to a data processing unit. The data processing unit further comprises a digital signal processing module that smoothens, transforms and filters the received acoustic signal. A statistical processing module further filters the acoustic signal from the data processing unit and generates a quantitative acoustic model for texture attributes such as hardness, fracturability, crispiness, etc. The quantitative model is correlated with a qualitative texture measurement from a descriptive expert panel. Texture of liquids are quantitatively measured with the quantitative acoustic model with the apparatus.

The present invention system may be utilized in the context of method of quantitatively measuring texture of a snack food, the method comprises the steps of:

(1) placing a liquid in a container on a moving or a non-movable surface;

(2) directing electromagnetic wave (energy) such as a laser to strike the liquid;

(3) generating an acoustic signal from the snack food;

(4) capturing the acoustic signal with an acoustic capturing device;

(5) forwarding the acoustic signal to a data processing unit; and (6) measuring the texture of the liquid with texture attributes from a texture model.

Integration of this and other preferred exemplary embodiment methods in conjunction with a variety of preferred exemplary embodiment systems described herein in anticipation by the overall scope of the present invention.

BRIEF DESCRIPTION OF THE DRAWINGS

For a fuller understanding of the advantages provided by the invention, reference should be made to the following detailed description together with the accompanying drawings wherein.

FIG. **6*a*** is a texture measuring apparatus comprising a parabolic dish shaped housing and an acoustic capturing device positioned within the dish, according to an exemplary embodiment of the present invention.

Figure 7:
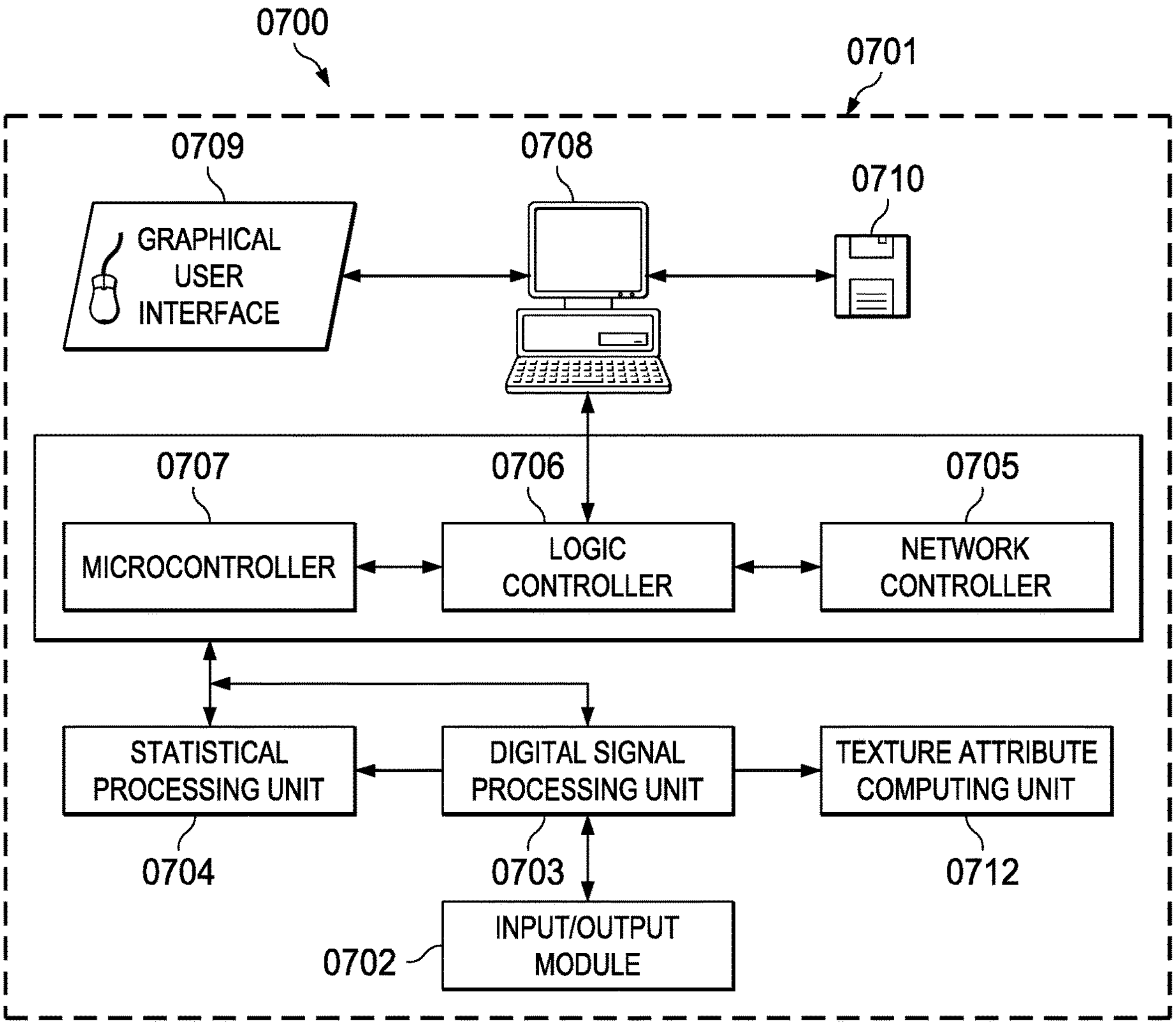

FIG. 7 is a data processing unit according to an exemplary embodiment of the present invention.

Figure 8:
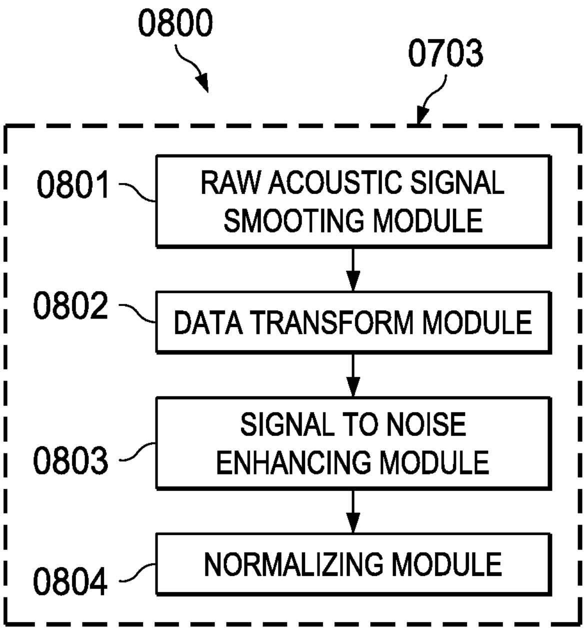

FIG. 8 is a digital signal processing unit according to an exemplary embodiment of the present invention.

Figure 9:
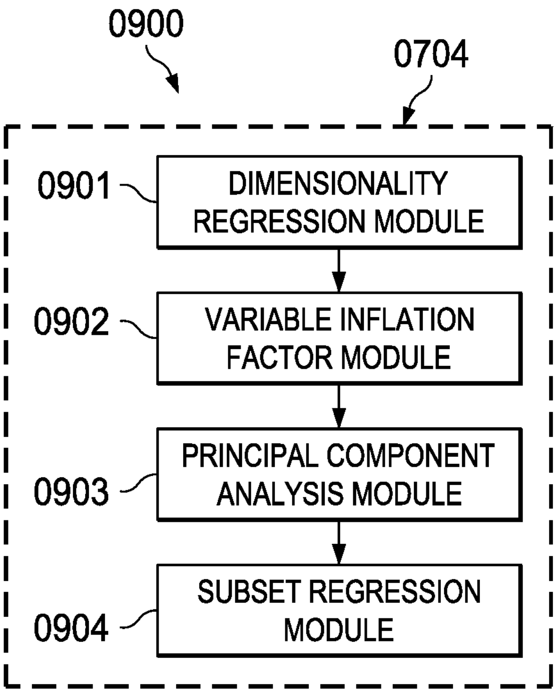

FIG. 9 is a statistical processing unit according to an exemplary embodiment of the present invention.

Figure 10:
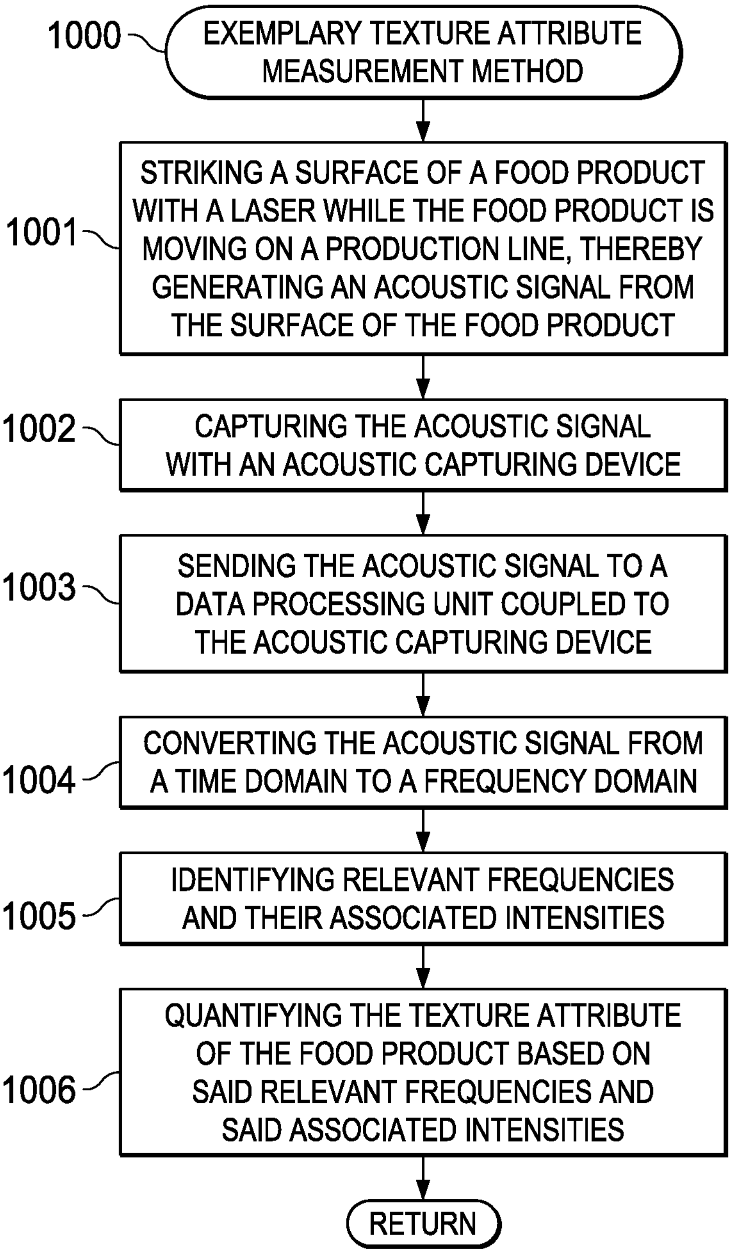

FIG. 10 is a flow chart method for quantitative measurement of texture according to an exemplary embodiment of the present invention.

Figure 11:
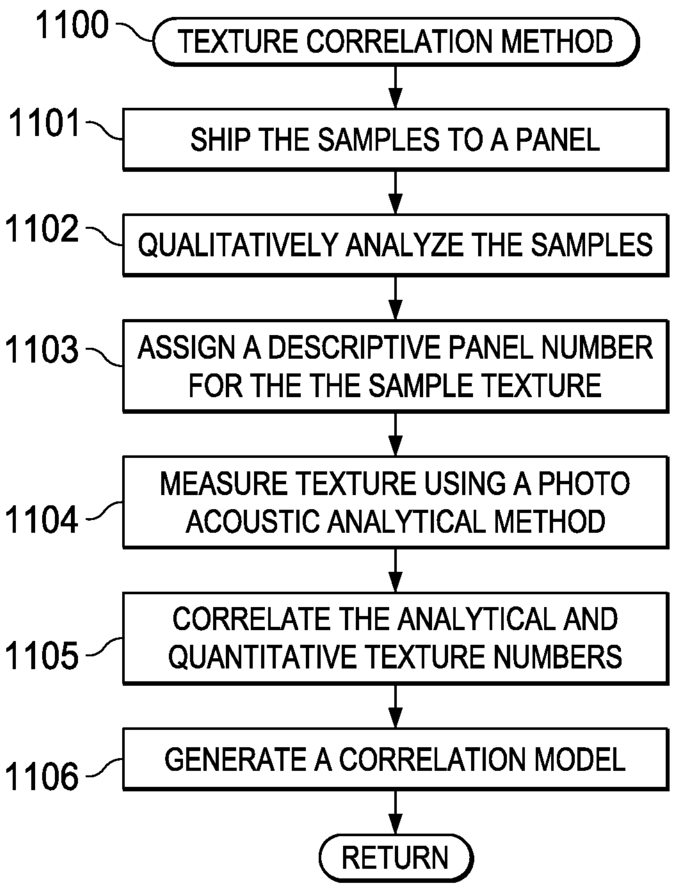

FIG. 11 is an exemplary flow chart method for quantitative correlation of texture according to a preferred embodiment of the present invention.

Figure 12:
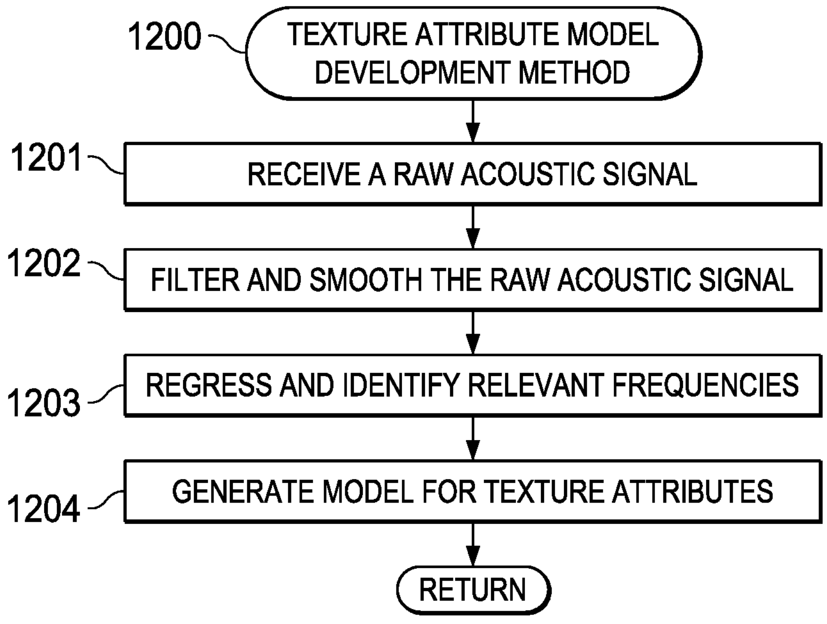

FIG. 12 is an exemplary flow chart method for quantitative texture model development according to a preferred embodiment of the present invention.

Figure 13:
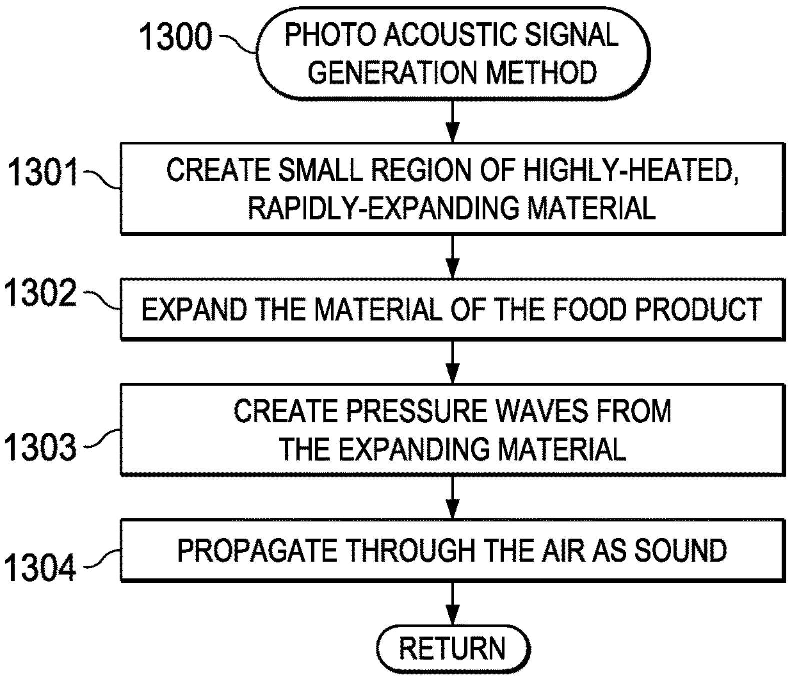

FIG. 13 is an exemplary flow chart method for photo acoustic signal generation according to a preferred embodiment of the present invention.

Figure 14:
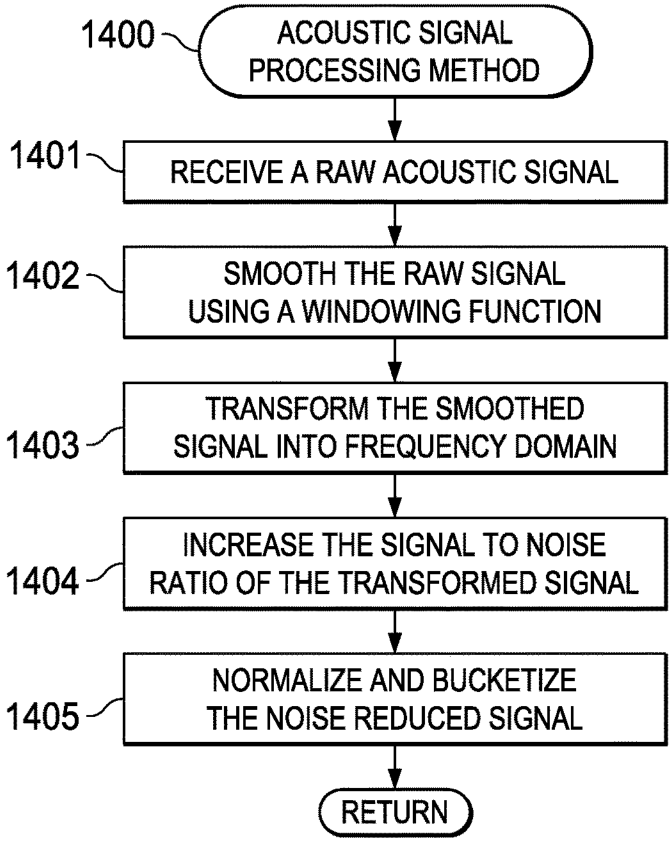

FIG. 14 is an exemplary flow chart method for acoustic signal processing according to a preferred embodiment of the present invention.

Figure 15:
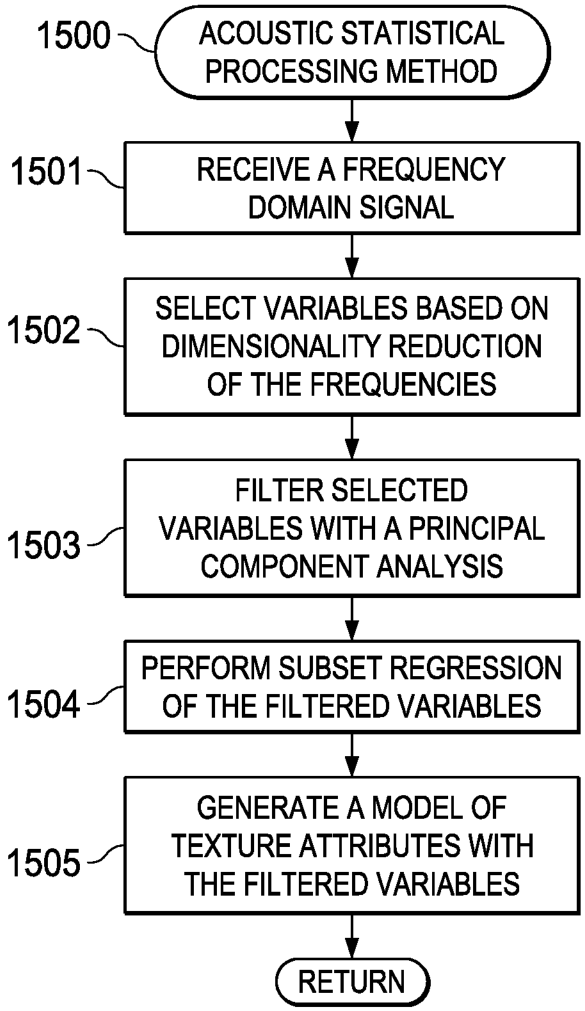

FIG. 15 is an exemplary flow chart method for acoustic statistical processing according to a preferred embodiment of the present invention.

Figure 16:
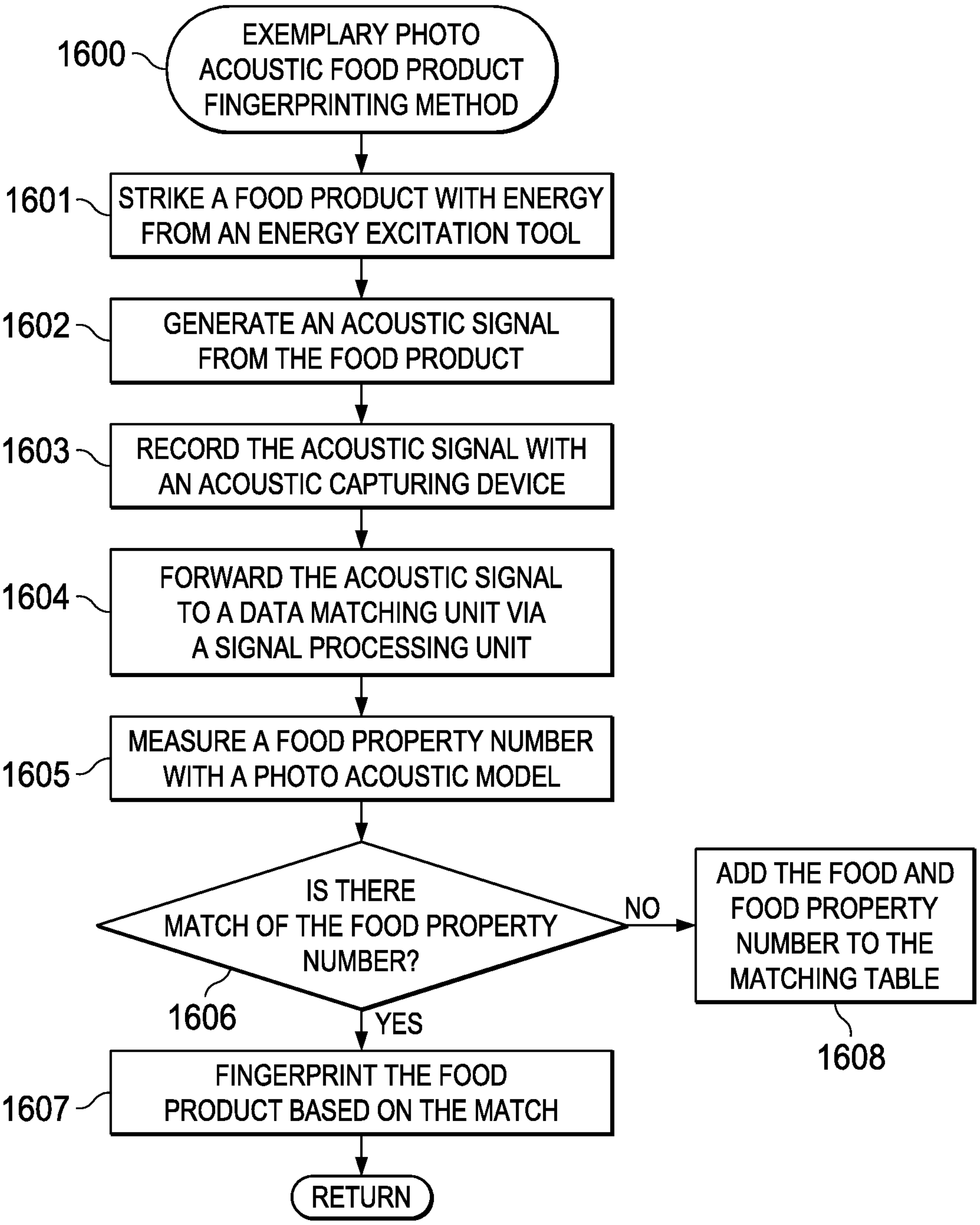

FIG. 16 is an exemplary food snack fingerprinting method according to a preferred exemplary embodiment.

FIG. 17 is an exemplary food snack fingerprinting matching table according to a preferred exemplary embodiment.

Figure 18:
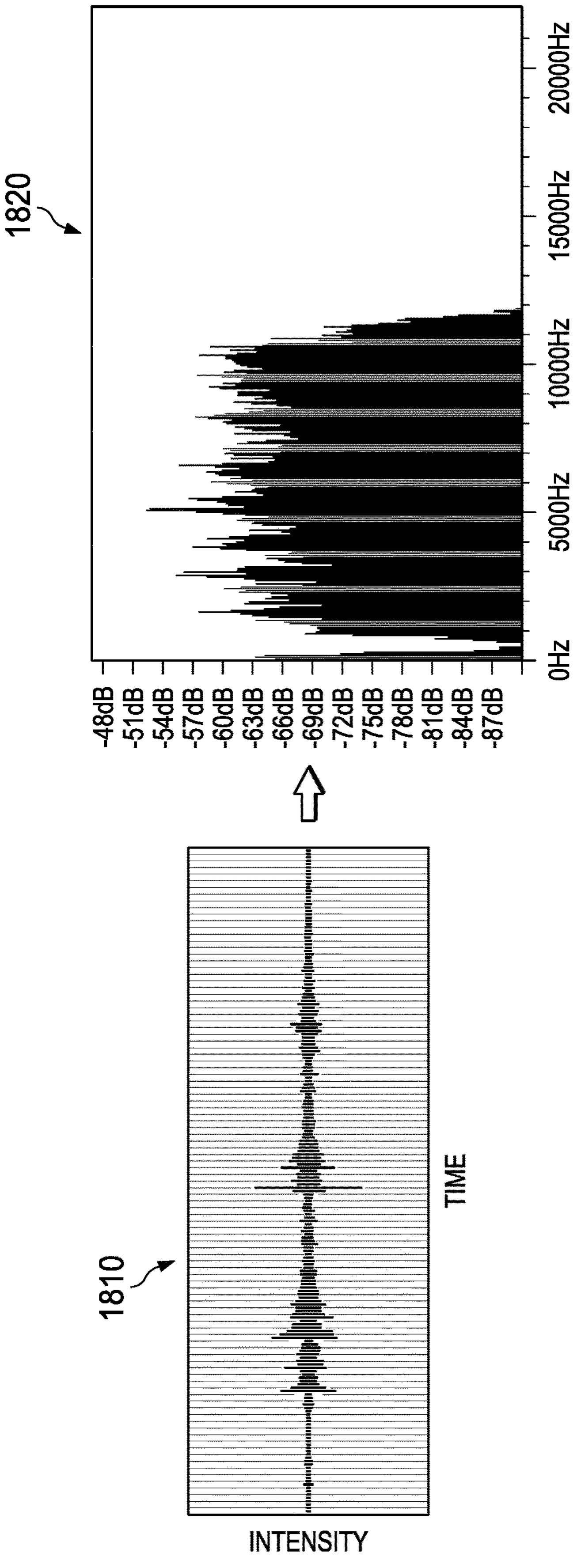

FIG. 18 is an exemplary acoustic signal time domain to frequency domain transformation chart according to a preferred embodiment of the present invention.

Figure 19:
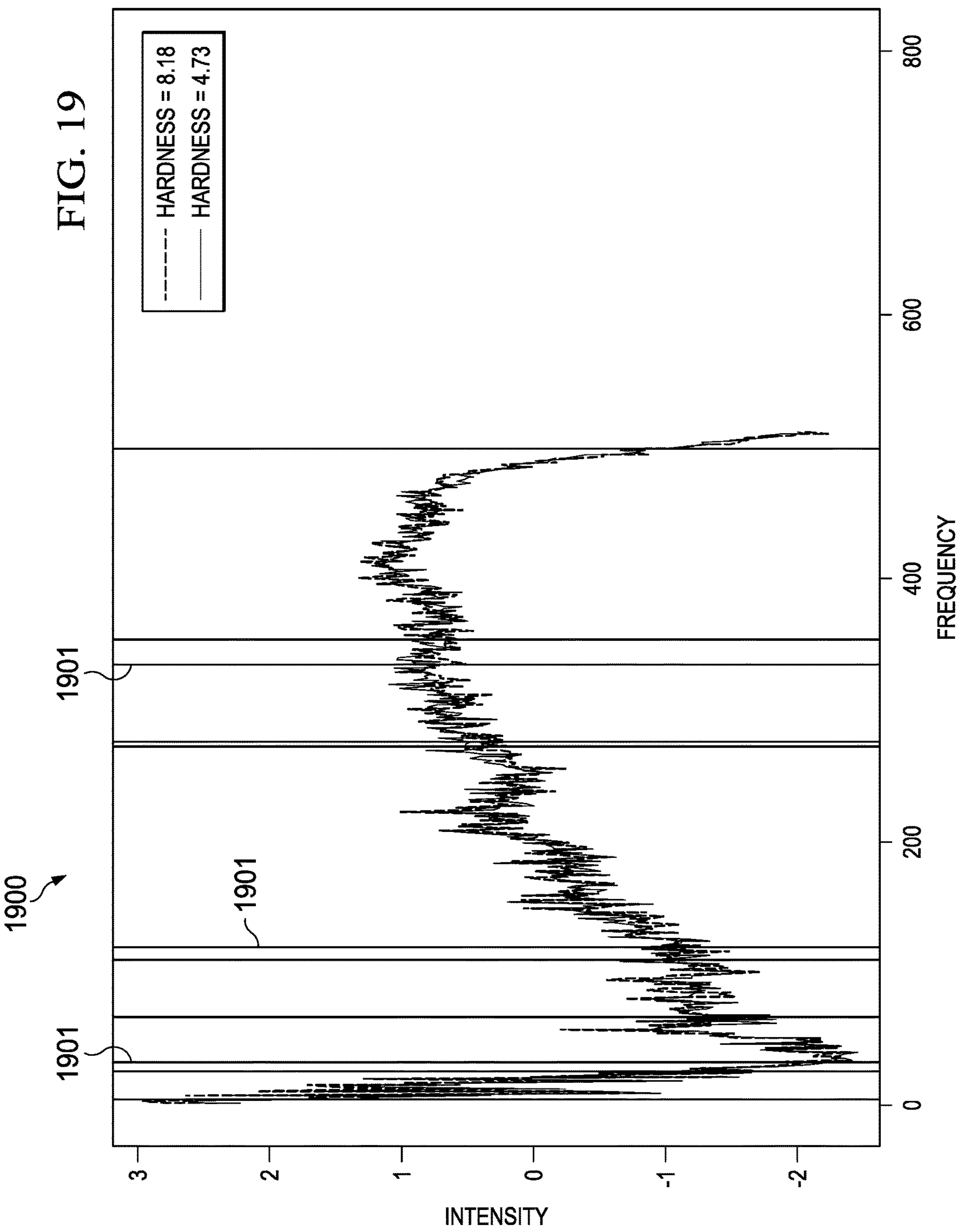

FIG. 19 is an exemplary texture attribute (hardness) vs. relevant frequencies chart according to a preferred embodiment of the present invention.

Figure 20:
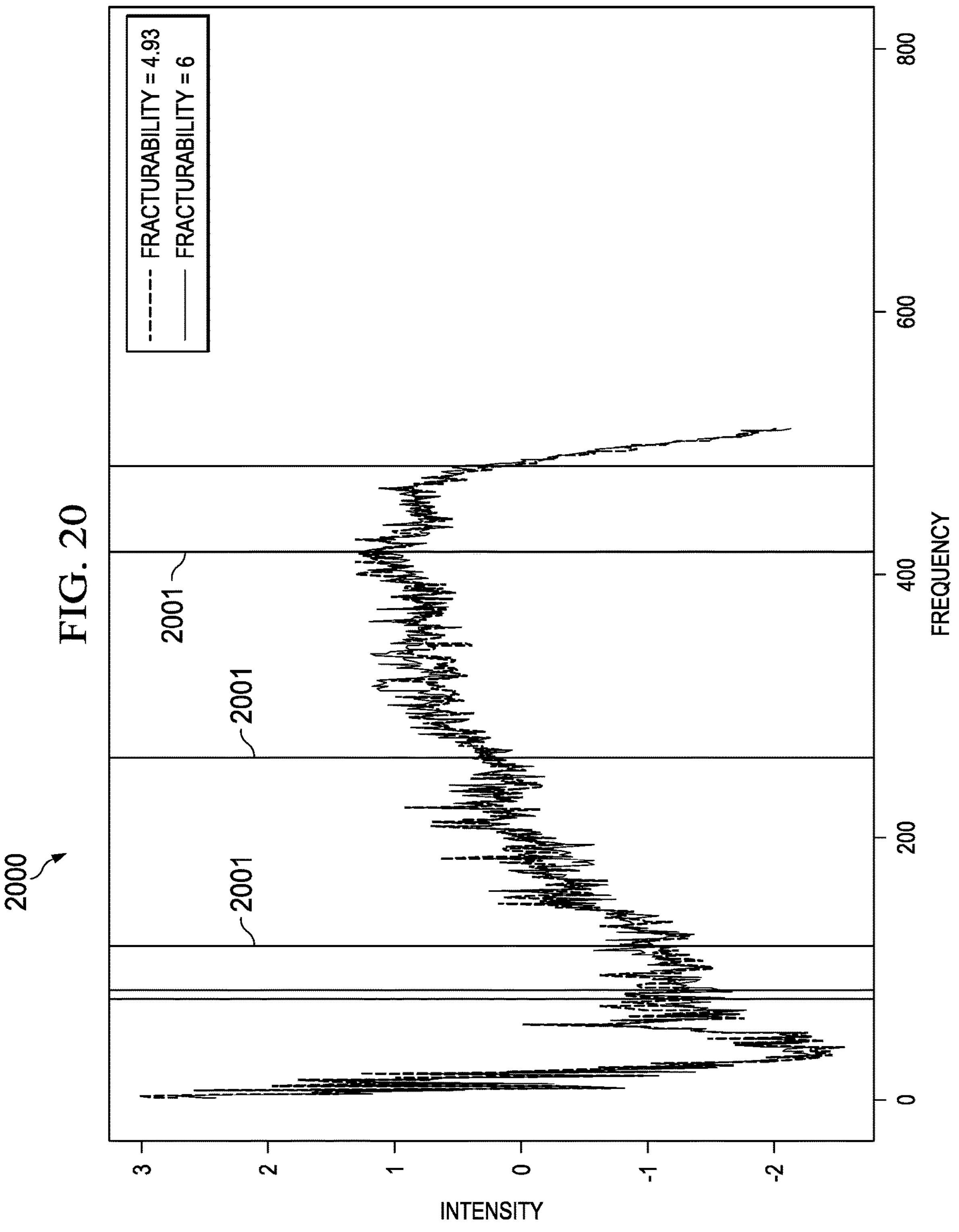

FIG. 20 is an exemplary texture attribute (fracturability) vs. relevant frequencies chart according to a preferred embodiment of the present invention.

Figure 21:
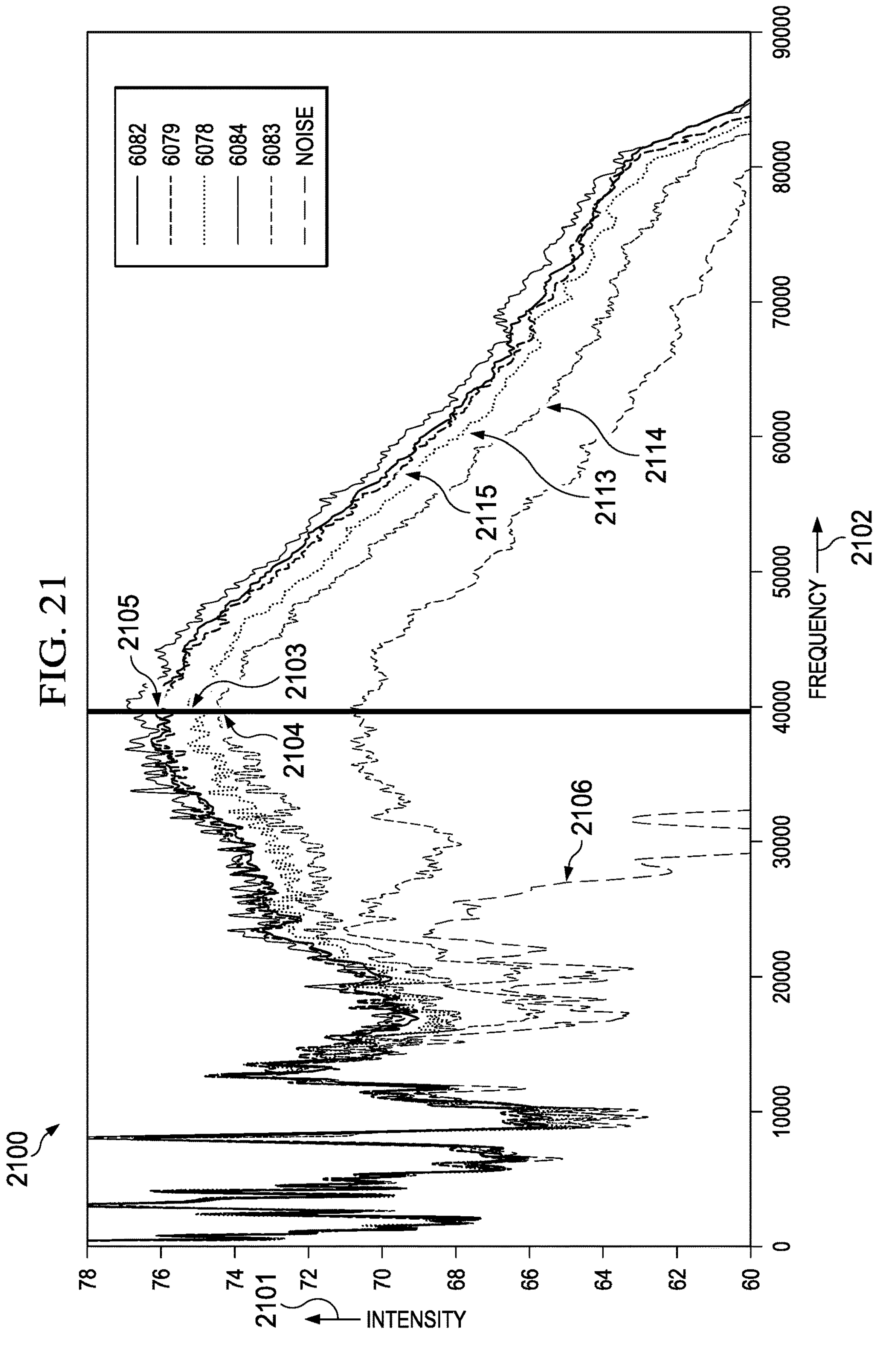

FIG. 21 is another exemplary texture attribute (hardness) vs. relevant frequencies chart according to a preferred embodiment of the present invention.

Figure 22:
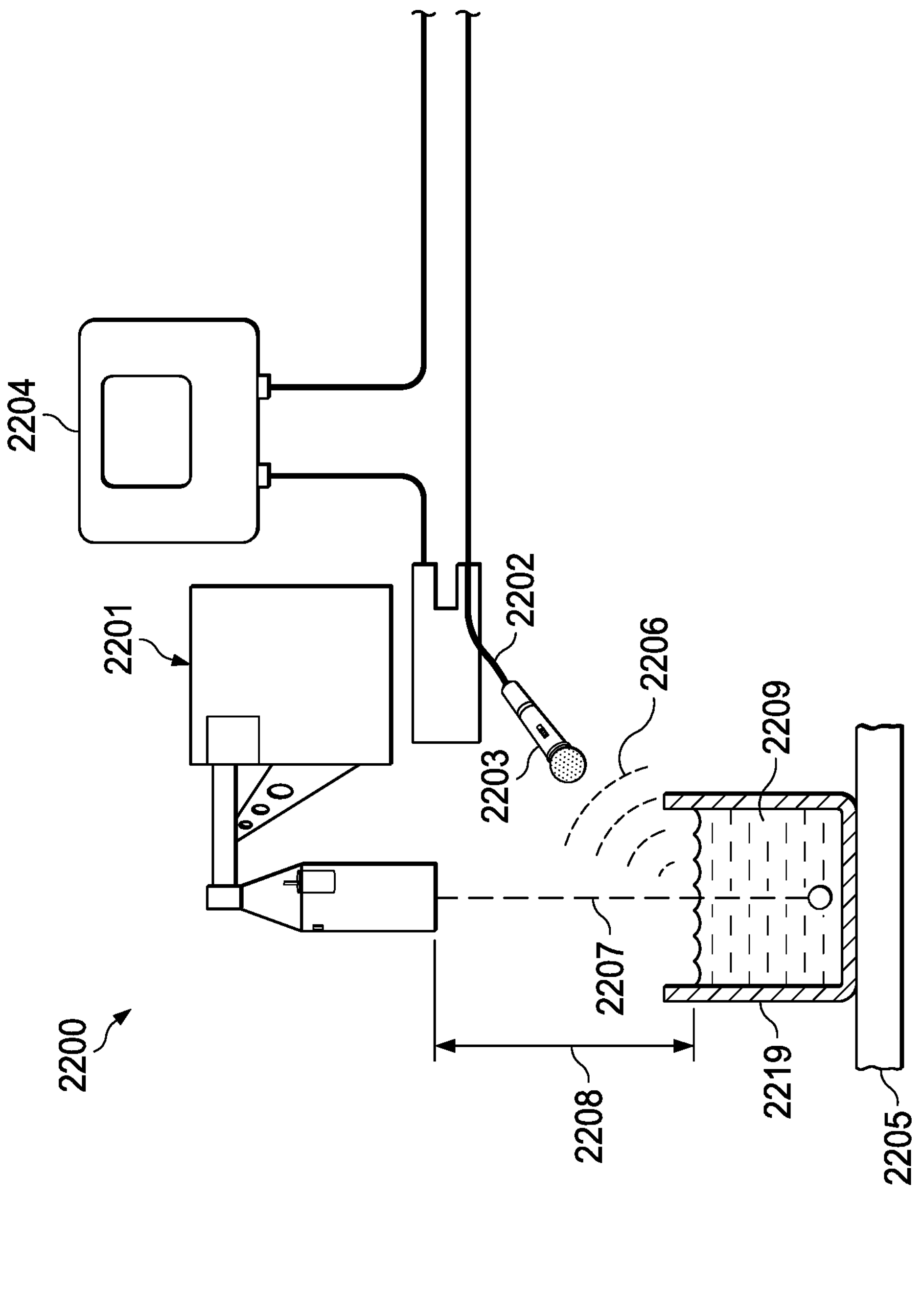

FIG. 22 is a system for quantitative measurement of texture attributes of a liquid according to an exemplary embodiment of the present invention.

Figure 23:
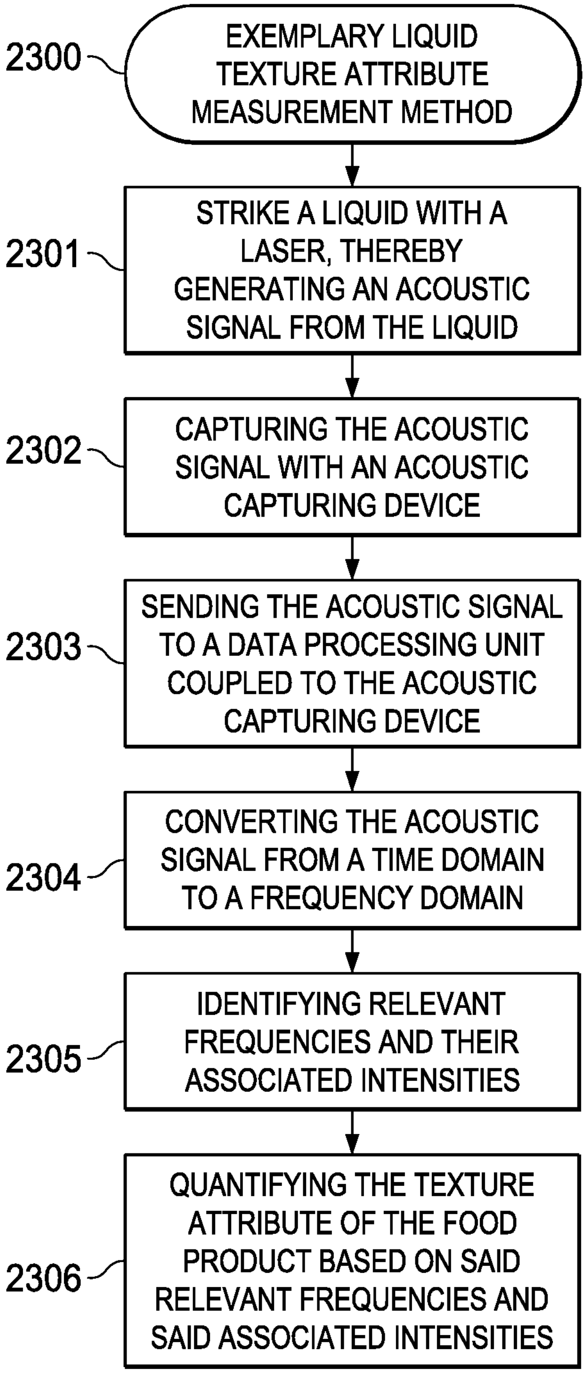

FIG. 23 is a flow chart method for quantitative measurement of a texture attribute of a liquid according to an exemplary embodiment of the present invention.

Figure 24:
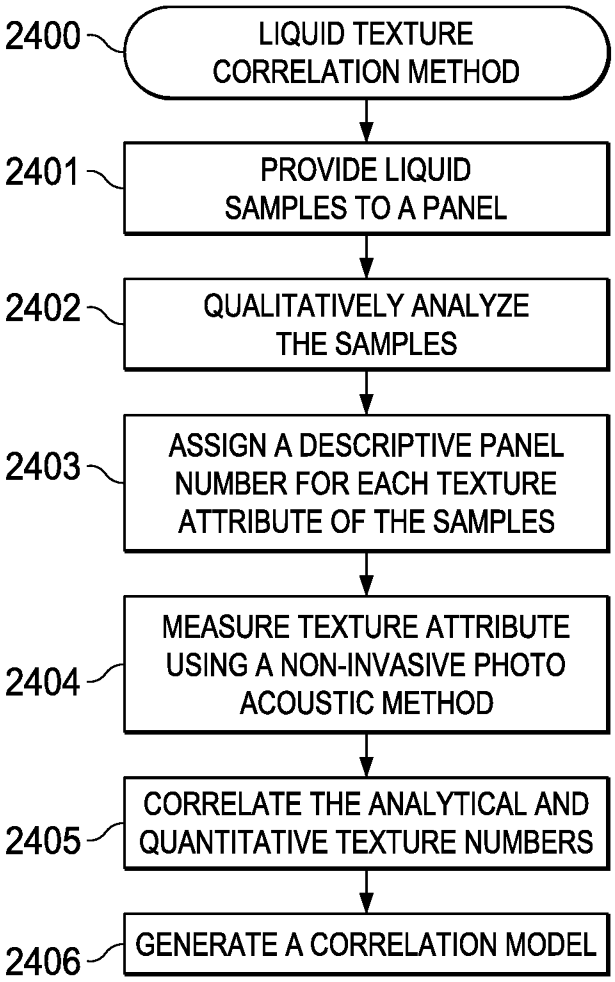

FIG. 24 is an exemplary flow chart method for quantitative correlation of a texture attribute of a liquid according to a preferred embodiment of the present invention.

Figure 25:
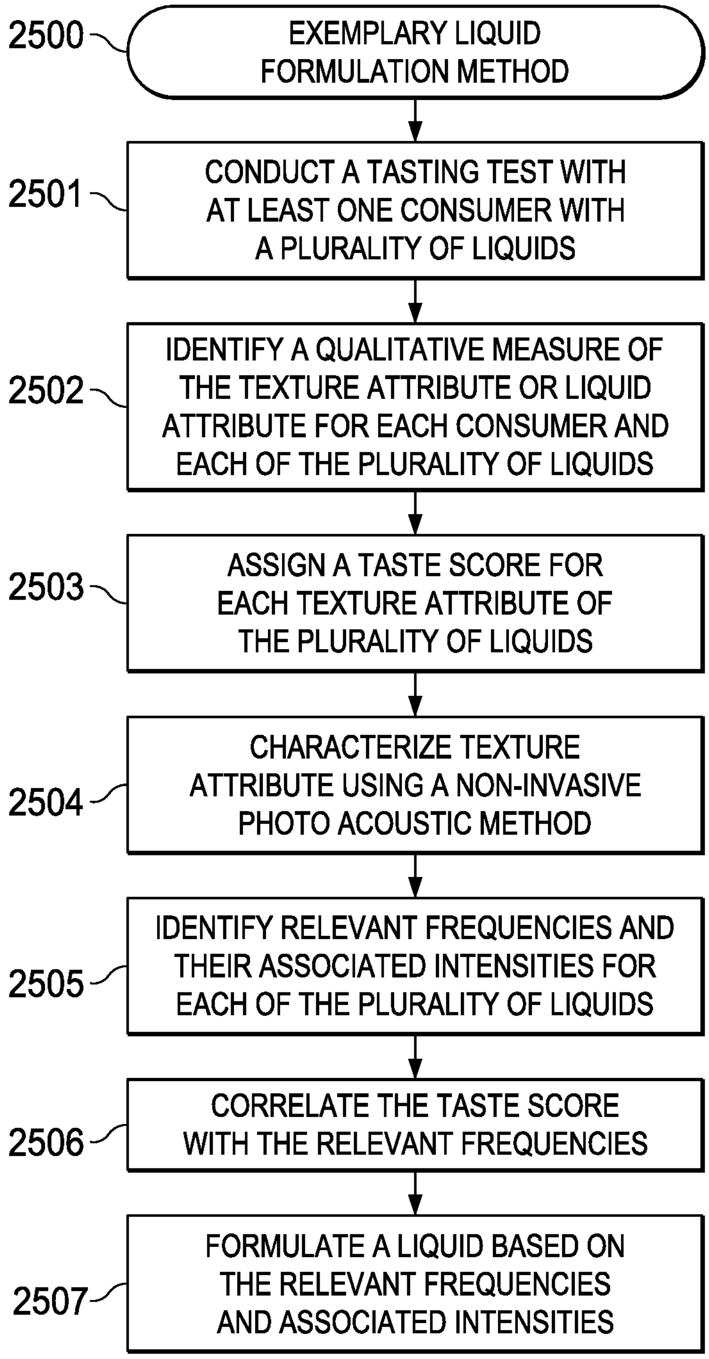

FIG. 25 is an exemplary flow chart method for formulating a beverage based on a photo acoustic correlation according to a preferred embodiment of the present invention.

Figure 26:
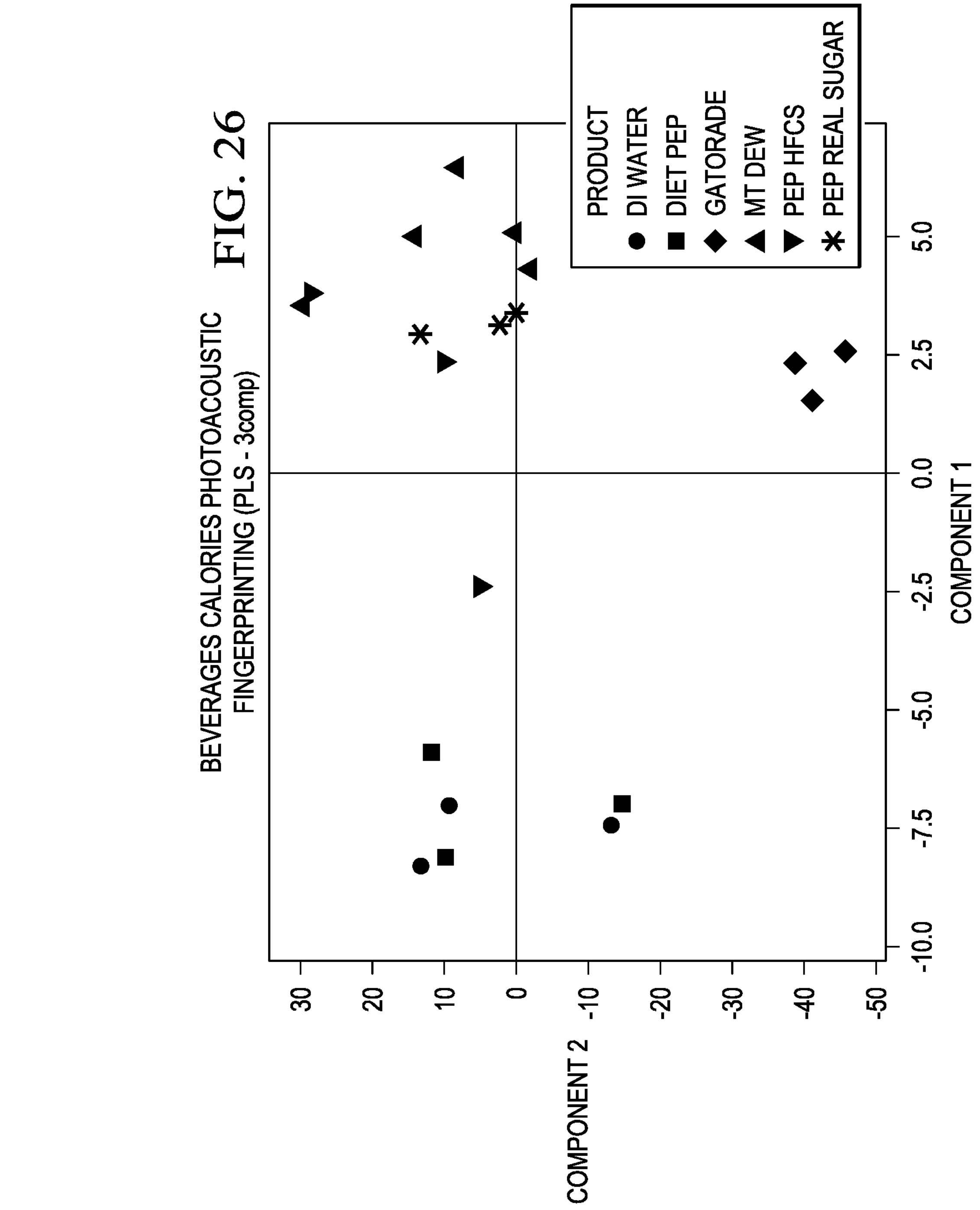

FIG. 26 is an exemplary statistical chart illustrating separation of liquids based on a quantitative texture attribute according to a preferred embodiment of the present invention.

DESCRIPTION OF THE PRESENTLY EXEMPLARY EMBODIMENTS

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently exemplary embodiment, wherein these innovative teachings are advantageously applied to quantitative measurement of texture attributes for food snacks apparatus and method. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

The term "texture" as used herein is defined as a property related to a number of physical properties of liquids such as viscosity, density, mouthfeel, astringency, mouth coating, sweetness, sensory, and rheology. It should be noted that the term "texture" and "texture attribute" is used interchangeably to indicate one or more properties of texture. It should be noted that the terms "descriptive panel number", "taste panel score", "qualitative texture number" and "taste panel number" are used inter-changeably to indicate a qualitative measurement of texture measurements by an expert panel. It should be noted that the terms "photo acoustic model" "acoustic model" "acoustic texture model" "quantitative texture attribute model" are used inter-changeably to indicate a quantitative model for a texture attribute of a food snack. It should be noted that the exemplary methods and apparatus applicable to food snacks as described herein may be applicable to liquids and vice versa.

Exemplary Embodiment System for Quantitative Measurement of Texture Attributes (0400-0900)

One aspect of the present invention provides a method to quantitatively measure the texture attributes of food snacks. Another aspect of the present invention involves correlating the quantitative texture attribute measurement to a qualitatively measured texture attribute by an expert panel. The present invention is also directed towards developing a texture attribute model based on relevant frequencies in a captured acoustic signal. According to yet another aspect of the present invention, food snacks are identified ("food finger printing") based on photo acoustic quantitative food snack property measurement.

Applicants herein have created a system that comprises an energy excitation tool for directing energy towards a liquid, an acoustic capturing device for recording/capturing an acoustic signal from the liquid and a data processing unit that processes the captured acoustic signal and generates a texture attribute model. In one embodiment, the energy excitation tool is a laser generating tool that is configured to generate a laser. There are a number of embodiments of this invention which fall within the scope of the invention in its broadest sense.

Exemplary Embodiment Texture Measurement Tool (0400)

Figure 1:
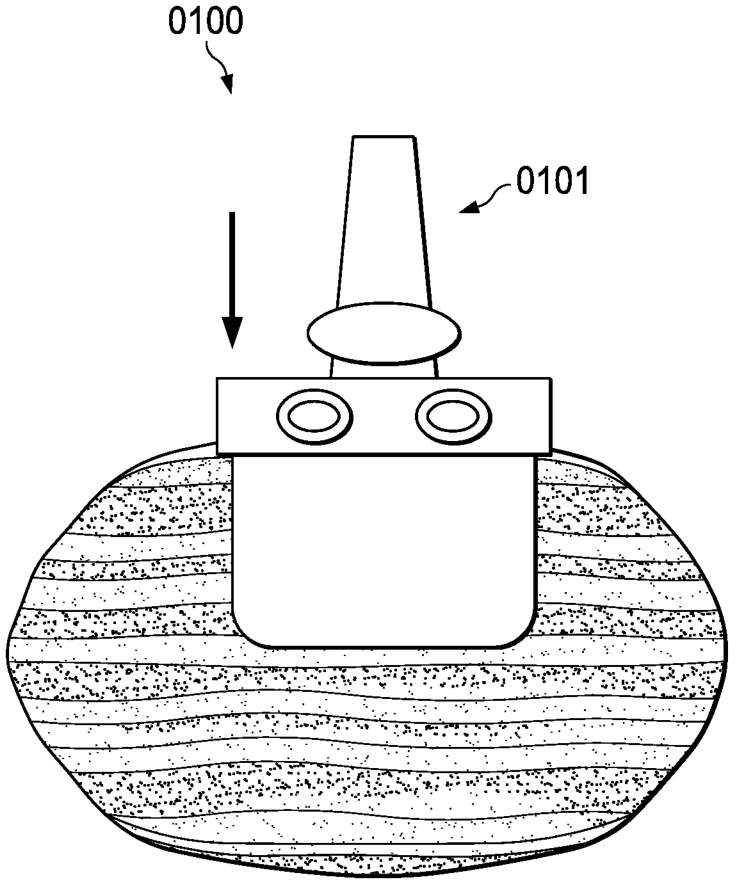
FIG. 1 is a prior art invasive system for measuring texture in food products.
Figure 2:
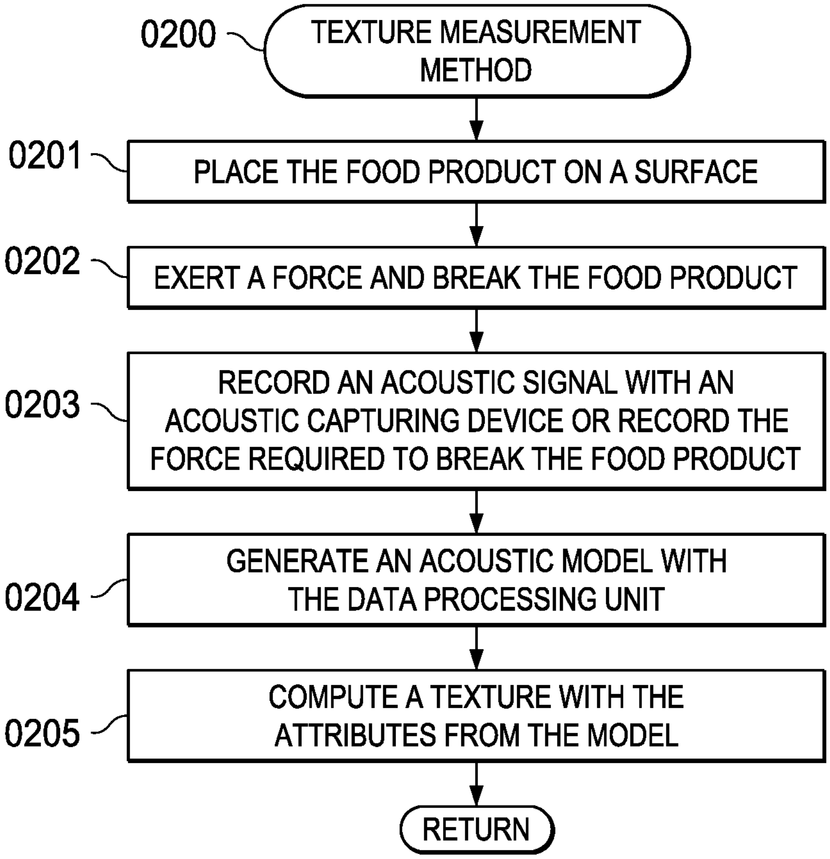
FIG. 2 is a prior art chart for measuring texture with acoustic signals.
Figure 3:
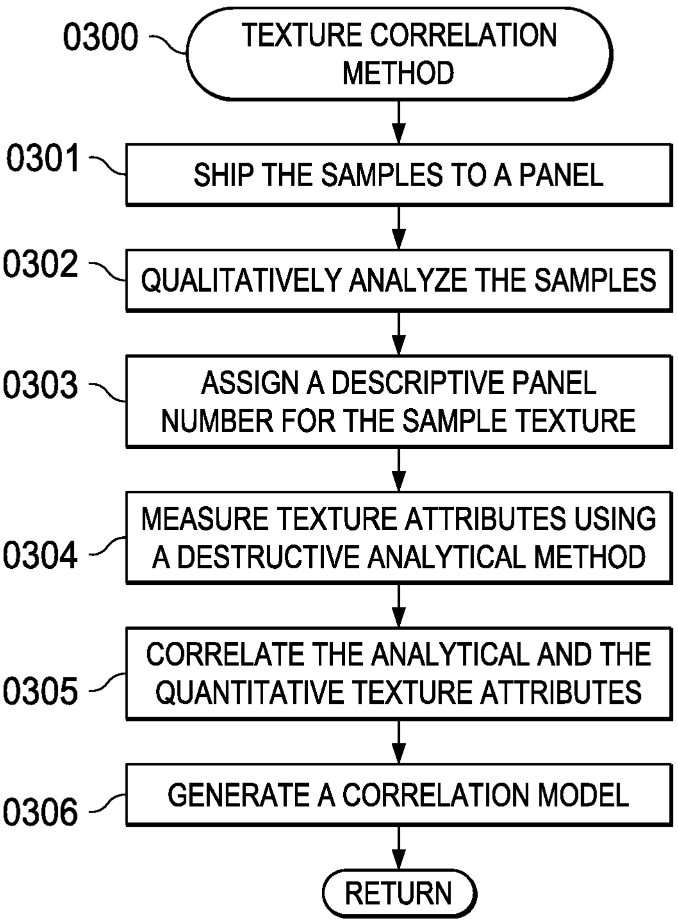
FIG. 3 is a prior art method for correlating texture measurements.
Figure 4:
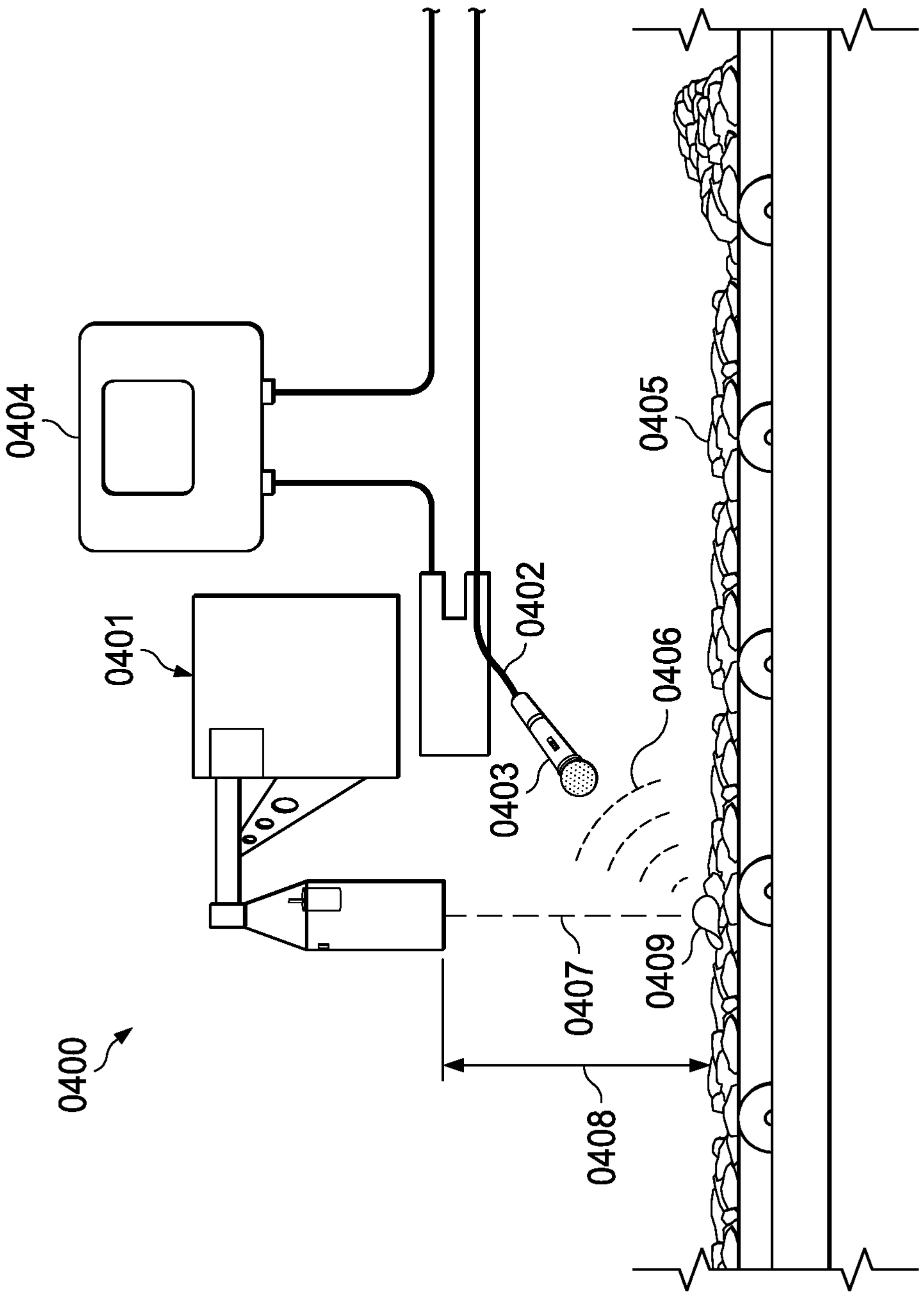
FIG. 4 is a system for quantitative measurement of texture attributes according to an exemplary embodiment of the present invention.

The present invention may be seen in more detail as generally illustrated in FIG. 4, wherein an exemplary texture measurement tool (0400) comprises a housing, an energy excitation tool (0401) that is attached to the housing and positioned to direct electromagnetic wave ("energy") such as a laser (0407) towards a food snack (0409) placed on a food staging station (0405). According to a preferred exemplary embodiment, the food snack is a starch based food snack. According to another preferred exemplary embodiment, the food snack is potato chips. The food staging station may be a movable or a non-movable surface. According to a preferred exemplary embodiment, the energy excitation tool is a laser generating unit that generates lasers. It should be noted that any tool that can generate excitation on a food substrate may be used as an energy excitation tool. The staging station (0405) may be a flat surface that is used for developing an acoustic model. The staging station (0405) may be a conveyor belt carrying the food snacks when texture is measured in a manufacturing process on-line. According to an exemplary embodiment, an acoustic capturing device (0403) may be positioned to record/capture an acoustic signal (0406) from the food snack (0409). The acoustic capturing device (0403) may be in communication with a data processing unit (DPU) (0404) via a cable (0402) or wirelessly. The acoustic capturing device may capture the acoustic signal across a wide range of frequencies 0 Khz to 500 Khz. Additionally, the acoustic capturing device (0403) may be placed at an angle directly above the food snack (0409). According to a preferred exemplary embodiment, the acoustic capturing device captures acoustic signals in a unidirectional manner. The acoustic capturing device may be in communication with a data processing unit. According to another preferred exemplary embodiment, the acoustic capturing device captures acoustic signals in omnidirectional manner. According to a preferred exemplary embodiment, the acoustic capturing device is a wireless microphone that contains a radio transmitter. In a preferred exemplary embodiment, the acoustic capturing device is a dynamic microphone. In another preferred exemplary embodiment, the acoustic capturing device is a fiber optic microphone. The acoustic capturing device (0403) may be placed at a pre-determined distance and a pre-determined angle from the food snack (0409). The pre-determined distance may be chosen such that it produces maximum energy density from the food snack. The distance (0408) from the bottom of energy excitation tool (0401) to the top of the staging station (0405) is selected so that the energy beam (laser) is safe within the manufacturing environment.

The acoustic capturing device (0403) may be connected physically with a conducting cable to the DPU (0404) via an input-output module in the DPU (0404). In an alternate arrangement, the acoustic capturing device (0403) may forward an acoustic signal to the input-output module in the DPU (0404) wirelessly. The wireless protocol may use standard protocols such as WIFI or Bluetooth. In an exemplary embodiment, the acoustic capturing device (0403) may be remotely located and the acoustic signal may be forwarded wirelessly to the DPU (0404) with a protocol such as LTE, 3G and/or 4G. In another exemplary embodiment, the remotely located DPU (0404) may be connected to the acoustic capturing device (0403) with wired protocol such as Ethernet.

The energy excitation tool (0401) is positioned to direct energy towards a food snack (0409). It should be noted that the angle of directing as shown is for illustration purposes only. The angle of directing the energy may be configured to produce an optimal excitation of the food snack such that an acoustic capture device (0403) may capture a complete acoustic signal after the excitation tool directs energy towards the food snack. The acoustic signal may then be captured for a period of time. The acoustic signal may be represented as Intensity (dB) vs. Time (secs). According to a preferred exemplary embodiment, the acoustic signal is captured for 1 sec to 5 minutes. According to yet another preferred exemplary embodiment, the acoustic signal from the food snack is captured for 2 sec. According to a more preferred exemplary embodiment, the acoustic signal from the food snack is captured for 1 sec. According to a most preferred exemplary embodiment, the acoustic signal from the food snack is captured for 10 sec.

According to a preferred exemplary embodiment, the energy excitation tool directs energy towards the food snack for a pulse duration or firing time of 5 nanoseconds to 5 minutes. According to yet another preferred exemplary embodiment, the energy excitation tool directs energy towards the food snack for 1 nanosecond. According to a more preferred exemplary embodiment, the energy excitation tool directs energy towards the food snack for 1 minute. According to a most preferred exemplary embodiment, the energy excitation tool directs energy towards the food snack for 9-12 nanoseconds.

Exemplary Energy Excitation Tool (0500)

Figure 5:
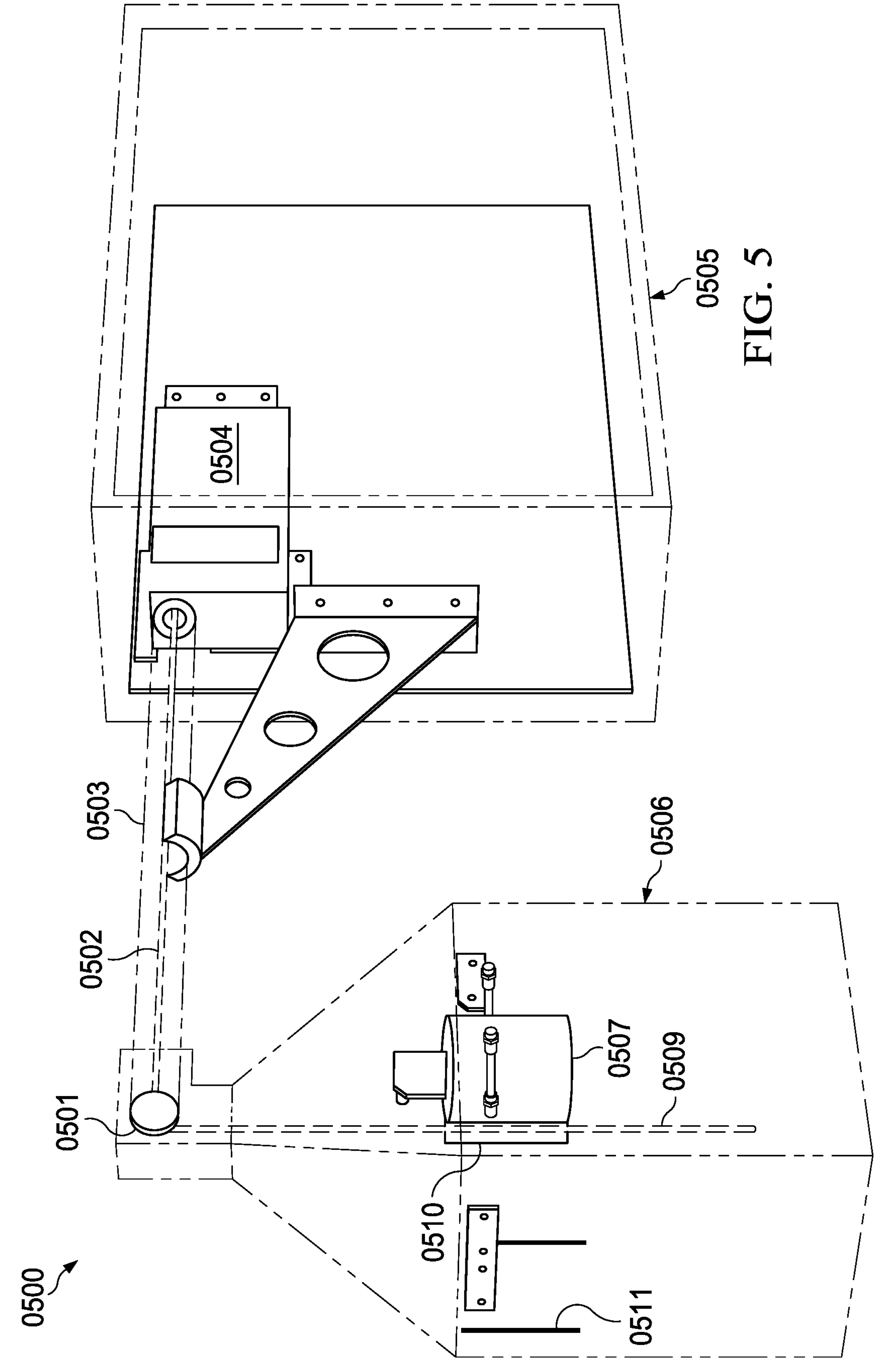
FIG. 5 is an excitation tool that directs energy on a food product according to an exemplary embodiment of the present invention.

As generally illustrated in FIG. 5 (0500), an exemplary energy excitation tool (0500) that is similar to (0401) in FIG. 4 (0400) comprises an energy generating unit (0504) that is mounted within an energy enclosure (0505). The energy generating unit (0504) may generate an electromagnetic wave that may excite molecules from a food substrate causing the molecules to gain heat energy and vibrate producing a sound. The electromagnetic wave may comprise a wavelength in the range of 512 nm to 2048 nm. A more preferred range of the electromagnetic wave may comprise a wavelength in the range of 470 nm to 1 mm. The energy generating unit (0504) may excite molecules from a food substrate causing the molecules to vibrate a produce sound. Excitation may be defined as an elevation in energy level above an arbitrary baseline energy state. When molecules are excited the thermal expansivity may be related to the type and density of material in accordance with the following equation. Texture may be indirectly related to thermal expansivity and therefore texture is indirectly related to the type and density of the material.

$$\alpha_V = \frac{1}{V}\frac{\partial(V)}{\partial T} = \frac{1}{\frac{1}{\rho}}\frac{\partial\left(\frac{1}{\rho}\right)}{\partial T} = \rho\frac{\partial(\rho^{-1})}{\partial T} = -\frac{\rho}{\rho^2}\frac{\partial(\rho)}{\partial T} = -\frac{1}{\rho}\frac{\partial(\rho)}{\partial T} = -\frac{\partial \ln(\rho)}{\partial T}$$

Thermal expansivity=function (material, density)

Texture=function (material, density)

A specific technical definition for energy level is often associated with an atom being raised to an excited state. The energy excitation tool, in a preferred exemplary embodiment, is a laser generating tool that produces a very narrow, highly concentrated beam of light. A laser is a device that emits light through a process of optical amplification based on the stimulated emission of electromagnetic radiation. Spatial coherence in the laser allows a laser to be focused to a tight spot. Spatial coherence also allows a laser beam to stay narrow over great distances (collimation). Lasers can also have high temporal coherence, which allows them to emit light with a very narrow spectrum, i.e., they can emit a single color of light. The energy generating unit (0504) ("laser generating unit") may include a gain medium, laser pumping energy, high reflector, output coupler and a laser beam. The laser beam (0502) may travel through a hollow tube (0503) and strike a mirror (0501). The hollow tube (0503) may be held by a metallic arm (0512) that is mechanically connected to the energy enclosure (0505). In a preferred exemplary embodiment, the laser beam may travel without the need for a hollow tube. The metallic arm may be made of a metal that may carry the weight of the hollow tube (0503) and the housing (0506). The laser may contain additional elements that affect properties of the emitted light, such as the polarization, wavelength, spot size, divergence, and shape of the beam.

The mirror (0501) reflects the laser beam (0502) towards a food snack substrate positioned on a surface. According to a preferred exemplary embodiment, the mirror is angled between 1 degree and 89 degrees to the vertical. According to a most preferred exemplary embodiment, the mirror is angled at 45 degrees to the vertical. Any combination of multiple mirrors, multiple lenses, and expanders may be used to produce a consistent spot size laser that strikes the food snack. The laser beam from the laser generating unit may be redirected, expanded and focused as the beam passes through a combination of mirrors and lenses. It should be noted that even though a single mirror and single lens are illustrated in FIG. 5, it should not be construed as a limitation and any combination of the mirrors, lenses and expanders may be used to produce a constant spot size laser beam. The reflected laser beam (0509) passes through a narrow window (0511) in a housing (0506). An acoustic device enclosure (0507) for housing an acoustic capturing device may be mounted in the housing (0506). It should be noted that the enclosure (0506) as illustrated in FIG. 5 (0500) is shaped as rectangular, however any shape may be used for the enclosure that is capable of being acoustically insulated and human safe. According to a preferred exemplary embodiment, the housing (0506) may be cylindrical, cubical, conical, spherical or triangular prism shaped. Similarly, acoustic device enclosure (0507) may be shaped as rectangular prism, cylindrical, cubical, conical, spherical, or triangular prism. The acoustic device enclosure (0507) may house an acoustic device such as a microphone. The acoustic device enclosure (0507) may also maintain a positive air pressure in order to ensure a particulate free environment within the enclosure (0507). The positive air pressure may be maintained by blowing air through the enclosure with an air pump. According to a preferred exemplary embodiment, the narrow window (0511) may be made out a sapphire material or fused silica. Any translucent window that separates the laser beam from the food product may be used as the narrow window. According to another preferred exemplary embodiment, the narrow window (0511) is aligned such that the laser beam (0509) is within +−1 degree to a desired direction. The desired direction may be vertical or at an angle to a vertical plane. A laser level sensor (0510) is positioned within the housing (0506) to sense the level of the food from the surface. The laser sensor (0501) may prevent humans from undesired entry into the housing (0506). For example, if the laser sensor detects an object or a human hand over the food snack, it may automatically shut off the laser and prevent from exposing the human to the laser. According to a preferred exemplary embodiment, the laser level provides for a human safe laser environment. According to another preferred exemplary embodiment, the laser level detects a food snack within +−2 inches from a staging surface. A temp sensor (0511) may be positioned within the housing (0506) to measure temperature. According to a preferred exemplary embodiment, a texture attribute measurement of the food product may be compensated for temperature fluctuations of the food product.

The laser beam from the laser generator may also be directed via fiber optic cable to the product bed, with any number of focusing and expanding optics coupled with the fiber optic cable in between the laser and the product. The fiber optic cable does not need to be parallel to the beam path, aside from end at which the laser beam enters the fiber optic cables.

Exemplary Energy Excitation Tool and Exemplary Acoustic Capturing Device (0600)

Figure 6:
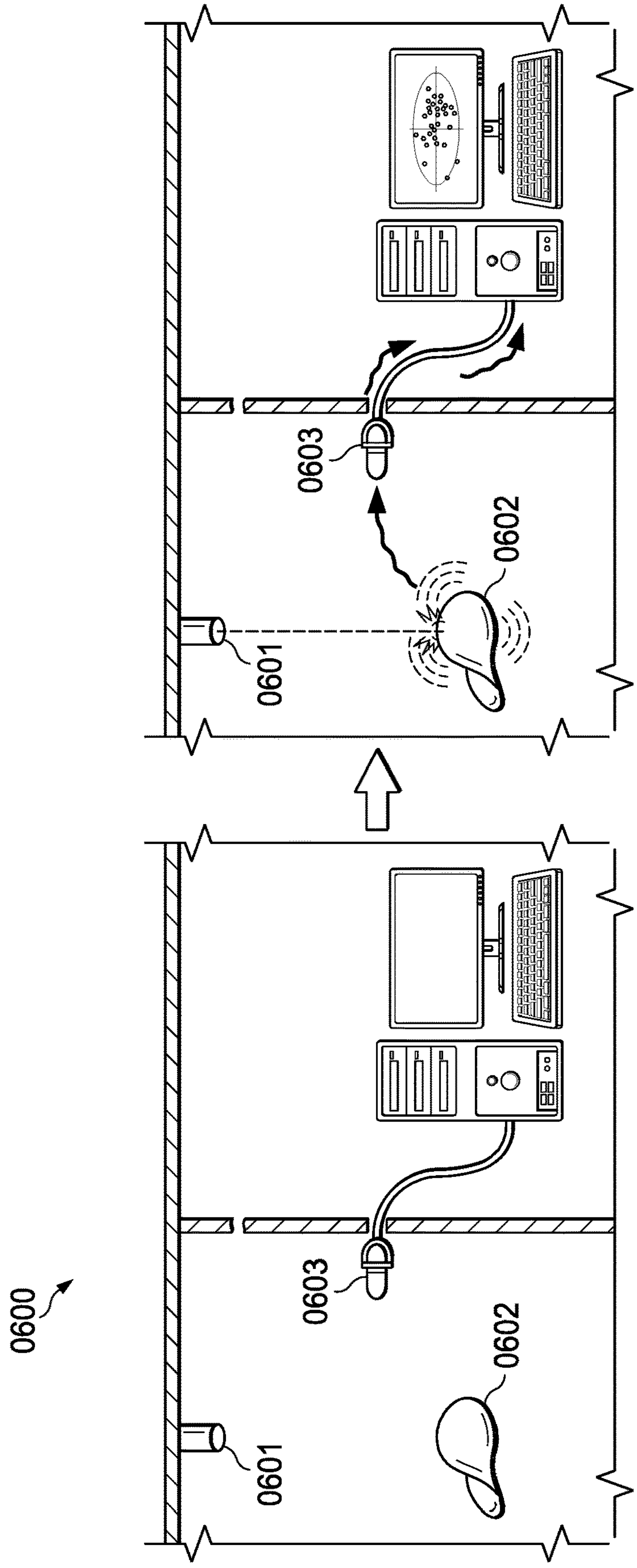
FIG. 6 is an acoustic capturing unit that captures an acoustic signal according to an exemplary embodiment of the present invention.

As generally illustrated in FIG. 6, a before and after energy excitation from an energy excitation tool is shown. The energy excitation tool (0601) is positioned to direct energy ("electromagnetic wave") towards a food snack (0602). It should be noted that the angle of directing as shown is for illustration purposes only. The angle of directing the energy may be configured to produce an optimal excitation of the food snack such that an acoustic capture device (0603) may capture a complete acoustic signal after the excitation tool directs energy towards the food snack. The acoustic signal may then be captured for a period of time. The acoustic signal may be represented as Intensity (dB) vs. Time (secs or micro secs). According to a preferred exemplary embodiment, the acoustic signal is captured for 1 sec to 3 minutes. According to yet another preferred exemplary embodiment, the acoustic signal from the food snack is captured for 10 sec. According to a more preferred exemplary embodiment, the acoustic signal from the food snack is captured for 1 sec. According to a most preferred exemplary embodiment, the acoustic signal from the food snack is captured for 10 seconds.

According to a preferred exemplary embodiment, the energy excitation tool directs energy towards the food snack for 1 sec to 3 minutes. According to yet another preferred exemplary embodiment, the energy excitation tool directs energy towards the food snack for 1 micro second. According to a more preferred exemplary embodiment, the energy excitation tool directs energy towards the food snack for 1 minute. According to a most preferred exemplary embodiment, the energy excitation tool directs energy towards the food snack for 10 seconds.

According to a preferred exemplary embodiment, fluence (energy per unit area) of the area at the product bed is between 15 mJ/mm2 and 700 mJ/mm2. According to a more preferred exemplary embodiment, fluence at the product bed is between 62.5 $mJ/mm^2$ and 594.5 $mJ/mm^2$. According to a yet another preferred exemplary embodiment, fluence at the product bed is between 300 $mJ/mm^2$ and 350 $mJ/mm^{2\prime}$ According to a most preferred exemplary embodiment, fluence at the product bed is 311 mJ/mm2. The fluence could be varied by changing the energy of the laser or the spot size (area) of the laser.

In order to achieve the most optimal energy density, the diameter of the laser beam may be customized from the laser generator. According to a preferred exemplary embodiment, the laser beam diameter ranges from 100 micrometers to 400 micrometers. According to a preferred exemplary embodiment, the laser beam diameter ranges from 250 micrometers to 350 micrometers. According to a preferred exemplary embodiment, the laser beam diameter is 300 micrometers. The diameter of the laser beam may be adjusted to ensure that maximum excitation energy density is achieved within a four inch window (+/−2 inches from center point). The point of impact of the laser beam on the product bed should ideally be at the beam's focal point (which is the point of highest energy density), or within +/−2 inches of the focal point according to a preferred exemplary embodiment. The apparatus may use mirrors and focusing lenses with an Anti-Reflective (AR) coating for 1064 nm wavelengths. An example of the beam and focusing mirror arrangement may be a beam that originates at the laser generator, strikes a turning mirror positioned 702 mm away, and reflects 400 mm downward to pass through a focusing optic, which is also Anti-Reflective coated for 1064 nm wavelengths. The beam may then pass through a final window that is designed to seal the optics away from the external environment and prevent any oil/debris build-up from forming on the optics. According to a preferred exemplary embodiment, a preferred spot size is achieved at 200 mm-600 mm away from the focusing optic. According to more a preferred exemplary embodiment, a preferred spot size is achieved at 300 mm-500 mm away from the focusing optic. According to most a preferred exemplary embodiment, a preferred spot size is achieved at 400 mm from the focusing optic.

The acoustic capturing device such as a microphone may be directionally pointed at the point of beam impact at the product bed and positioned such that it is no more than 2 feet away. According to a preferred exemplary embodiment, the acoustic capturing device is positioned in between 1 inch and 2 feet from the point of beam impact on the food product. According to a preferred exemplary embodiment, the acoustic capturing device is positioned in between 1 inch and 1 foot from the point of beam impact on the food product. According to a preferred exemplary embodiment, the acoustic capturing device is positioned in between 1 feet and 2 feet away from the point of beam impact on the food product.

Figure 6A:
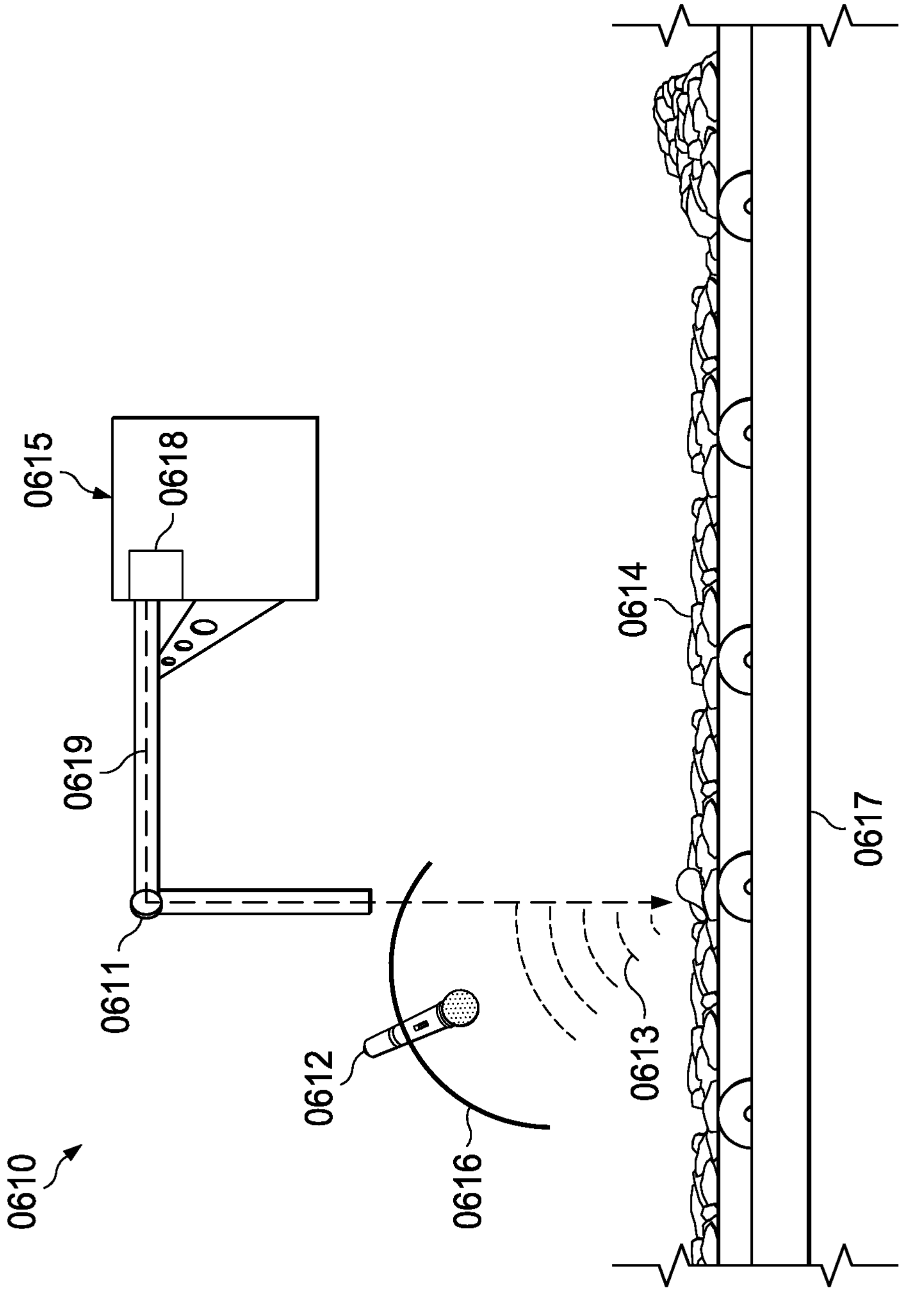

According to another preferred exemplary embodiment, the housing may be shaped cylindrical. According to yet another preferred exemplary embodiment, the housing may be shaped as a parabolic dish. As generally illustrated in FIG. 6*a* (0610), a laser beam generator (0618) housed within an energy enclosure (0615) generates a laser beam (0619). The laser beam may be reflected from a mirror (0611) and thereafter strike a food product (0614) that may be passing on a movable surface such as a conveyor belt (0617). When the laser beam strikes the food product, an acoustic signal may be generated. An acoustic capturing device (0612) such as a microphone may be positioned within a housing (0616) to capture an optical signal (0613) with maximum energy density. The acoustic capturing device (0612) such as a microphone may be centered at a parabolic dish, which would direct the acoustic signals to the microphone. A temp sensor may be positioned within the housing (0616) to measure temperature of the food product. According to a preferred exemplary embodiment, a texture attribute measurement of the food product may be compensated for temperature fluctuations of the food product.

Exemplary Data Processing Unit (0700)

As generally illustrated in FIG. 7 (0700), a data processing unit (DPU) (0701) comprises a control unit, a display unit, a processing unit and an input output module. The control unit may further comprise a microcontroller (0707), a logic controller (0706), and a network controller (0705). The display unit may be connected to the control unit via a host bus. The display unit may further comprise a display terminal (0708) that is configured to display a graphical user interface (GUI) (0709). The GUI (0709) may be navigated with a pointing device or through a keyboard connected to the DPU. The GUI (0709) may be used to input parameters such as food snack specific frequencies, acoustic capture time, acoustic capture frequency range The processing unit may include a digital signal processing unit (0703) and a statistical processing unit (0704). The digital signal processing unit (0703) may get input from an input-output module (0702). The statistical processing unit (0704) may receive input from the digital processing unit (0703) and further process the input to find relevant frequencies for generating a quantitative acoustic model for a food snack. When an acoustic capturing device captures an acoustic signal, the signal may be forwarded to the DPU (0701) via the input-output module (0702). The input output module (0702) may further comprise a customized hardware such an analog to digital convertor (ADC) for capturing and processing a captured acoustic signal. The acoustic signal may be forwarded to the DPU using a wired or a wireless connection. The connection protocol and connecting conducting wires may be chosen such that there is minimum loss of signal and the signal to noise ratio is acceptable for further processing. A general purpose bus may carry data to and from different modules of the DPU (0701). It should be noted that the operation of the bus is beyond the scope of this invention.

The microcontroller (0707) may perform instructions from a memory or a ROM (0710). The instruction set of the microcontroller may be implemented to process the data of the acoustic signal. A custom instruction set may also be used by the microcontroller to prioritize and expedite the processing of the acoustic signal in real time during a manufacturing operation. The customization of the instruction set is beyond the scope of this invention. The logic controller may perform operations such as sequencing, prioritization and automation of tasks. The logic controller may also oversee the hand shake protocol for the bus interface. According to an exemplary embodiment, the logic controller controls the logic for identifying relevant frequencies in an acoustic signal. The logic controller may comprise a matching module that contains predefined frequencies for a plurality of food snacks. The logic controller may subsequently match the captured frequencies in the acoustic signal and quickly determine the texture of the food snack and the quality of the texture. For example, the matching module may include specific frequencies such as 14000 Hz and 75000 Hz. When a recorded acoustic signal comprises the frequencies 14000 Hz or 75000 Hz, then the logic controller may determine a match and alert the microcontroller with an interrupt signal. The microcontroller may then display the texture information on the display (0708) via GUI (0709). The logic controller may further continuously monitor the state of input devices and make decisions based upon a custom program to control the state of output devices.

Exemplary Digital Signal Processing Module (0800)

Similar to the digital signal processing unit (0703) shown in FIG. 7 (0700), a digital signal processing unit (DSP) (0800) is generally illustrated in FIG. 8 (0800). The DSP (0800) may further comprise a smoothing module (0801), a data transformation module (0802), a signal to noise enhancing module (0803) and a normalization module (0804).

According to an exemplary embodiment, the acoustic smoothing module (0801) receives input from an input-module in a data processing unit and smoothens the received raw acoustic signal. Acoustic signals are inherently noisy and the data is discrete. The acoustic signals may be represented as Intensity (dB) vs. Time (secs or micro seconds). The data is made continuous by applying a windowing function to the discrete data. Windowing functions that may be applied to the discrete data may include Barlett, Blackmon, FlatTop, Hanning, Hamming, Kaiser-Bessel, Turkey and Welch windowing functions. A smoothing window with good frequency resolution and low spectral leakage for a random signal type may be chosen to smoothen the data. It should be noted that any commonly known windowing function may be applied to a raw acoustic signal to smoothen and interpolate the raw acoustic data.

The smoothened acoustic signal from the smoothing module (0801) may be forwarded to a data transformation module (0802). The data transformation module (0802) may transform the acoustic signal represented in time domain as Intensity (dB) vs. Time (secs) to frequency domain as Intensity (dB) vs. Frequency (Hz) as generally shown in FIG. 18 (1800). According to a preferred exemplary embodiment, the transformation of acoustic signal from a time domain representation to a frequency domain representation provides for accurately correlating texture attributes to the pertinent frequencies of a food snack. Combining multiple acoustic waves produces a complex pattern in the time domain, but the transformed signal using FFT clearly shows as consisting almost entirely of distinct frequencies. According to most preferred exemplary embodiment, a fast fourier transformation (FFT) technique may be used to transform the acoustic signal from a time domain representation to a frequency domain representation. An example of the transformation may be generally seen in FIG. 18 (1800).

The transformed frequency signal from the transformation module may be noisy. A signal to noise enhancement module (0803) may receive the transformed signal from the data transform module (0802) and enhance the signal-to-noise ratio of the signal for further processing. A technique for smoothing the data to increase the signal-to-noise ratio without greatly distorting the signal may be used. A process such as convolution may also be used to increase the signal-to-noise ratio. The convolution process may fit successive sub-sets of adjacent data points with a low-degree polynomial by the method of linear least squares. Normalization module (0804) may receive the enhanced signal-to-noise frequency domain signal from the signal to noise enhancement module (0803).

The DSP (0800) may also identify pertinent frequencies and associated intensities from the enhanced signal-to-noise frequency domain signal and store the information in a database. A texture attribute computing unit (0712) in the DPU (0701) may further retrieve the stored frequency and intensity information to compute a texture attribute of a food snack. After a photo acoustic model has been developed, the texture attribute computing unit (0712) may store coefficients for different food snacks. The texture attribute computing unit (0712) may then retrieve the stored coefficients and the stores frequency and intensity information to compute a texture attribute measurement or to fingerprint a food snack.

Exemplary Statistical Processing Unit (0900)

Similar to the statistical processing unit (0704) shown in FIG. 7 (0700), a statistical processing unit (SPU) (0900) is generally illustrated in FIG. 9. The SPU (0900) may further comprise a dimensionality regression module (0901), a variance inflation factor module (0902), a principal component analysis module (0903), and a subset regression module (0904).

The smoothened, transformed and normalized signal from the digital signal processing unit (0703) is forwarded to SPU (0704) for developing texture attribute model with good correlation. The high dimensionality of spectral data requires statistical filtering to build meaningful models. For example, the acoustically smoothed signal may be sampled at 512 linearly spaced frequencies, and each value may be averaged across replicates and used to create a statistical model. According to a preferred exemplary embodiment, the dimensionality regression module reduces the total frequencies of the spectral data to a reasonably acceptable number for model development with high correlation. According to another preferred exemplary embodiment, dimensionality reduction of the frequencies for variable selection is done using n the foregoing example, the total frequencies may be reduced from 512 to 18.

The data from the dimensionality regression module (0901) may be processed with a Variance inflation factors module (VIF) (0902). The VIF module measures how much the variance of the estimated regression coefficients are inflated as compared to when the predictor variables are not linearly related. The VIF is used to describe how much multicollinearity (correlation between predictors) exists in a regression analysis. As it is known, Multicollinearity is problematic because it can increase the variance of the regression coefficients, making them unstable and difficult to interpret. The square root of the variance inflation factor indicates how much larger the standard error is, compared with what it would be if that variable were uncorrelated with the other predictor variables in the model. For Example, if the variance inflation factor of a predictor variable were 5.27 ($\sqrt{5.27}=2.3$) this means that the standard error for the coefficient of that predictor variable is 2.3 times as large as it would be if that predictor variable were uncorrelated with the other predictor variables.

The data from variance inflation factors module (VIF) (0902) may further be processed with a principal component analysis module (0903). Principal component analysis (PCA) is a technique used to emphasize variation and bring out strong patterns in a dataset. It's often used to make data easy to explore and visualize. As defined in the art, Principal component analysis (PCA) is a statistical procedure that uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it is orthogonal to (i.e., uncorrelated with) the preceding components. According to a preferred exemplary embodiment, a principal components analysis is used to determine most relevant frequencies in the acoustic signal for developing a quantitative acoustic texture model. It should be noted that any other analysis technique known in the art may be used to identify principal components such as the relevant frequencies.

The data from the PCA module (0903) is further regressed with a best subsets regression module (0904) which is used to determine which of these most relevant frequencies are best for texture attribute model building with good correlation. An $R^2$ value greater than 0.9 may be considered a good correlation between the measure value from the model and descriptive expert panel number.

Exemplary Texture Attribute Measurement Method (1000)

As generally shown in FIG. 10, an exemplary texture measurement method may be generally described in terms of the following steps:

(1) striking a surface of a food product with a laser while the food product is moving on a production line, thereby generating an acoustic signal from the surface of the food product (1001);

(2) capturing the acoustic signal with an acoustic capturing device (1002);

(3) sending the acoustic signal to a data processing unit coupled to the acoustic capturing device (1003);

(4) converting the acoustic signal from a time domain to a frequency domain (1004);

acoustic signal is captured for a period of time and the signal is plotted as Intensity (dB) vs. Time (seconds)

(5) identifying relevant frequencies and their associated intensities (1005); and (6) quantifying the texture attribute of the food product based on said relevant frequencies and said associated intensities (1006).

This general method summary may be augmented by the various elements described herein to produce a wide variety of invention embodiments consistent with this overall design description.

Exemplary Texture Attribute Correlation Method (1100)

As generally shown in FIG. 11, an exemplary texture correlation method may be generally described in terms of the following steps:

(1) shipping food snack samples to an expert panel (1101);

The shipping of the food snack samples may take time and the food snack may undergo texture change during the shipping process. The number of times samples are shipped to an expert panel is substantially reduced due a high correlation model developed according to a preferred exemplary embodiment.

(2) Qualitatively analyzing the food snack samples (1102);

quantitatively measure texture attributes by an expert panel for assigning taste panel scores.

(3) Assigning a descriptive panel number for the texture attributes of the food snack sample (1103);

(4) Measuring texture attributes using a non-invasive acoustic analytical method (1104);

(5) Correlating the analytical and the qualitative texture attributes (1105); and (6) Generating a correlation model for the texture attributes (1106). The adjusted $R^2$ of the correlation is targeted to be greater than 0.9.

This general method summary may be augmented by the various elements described herein to produce a wide variety of invention embodiments consistent with this overall design description.

Exemplary Texture Attribute Model Development Method (1200)

As generally shown in FIG. 12, an exemplary texture attribute model development method may be generally described in terms of the following steps:

(1) Receiving a raw acoustic signal (1201);

(2) Filtering, smoothing and transforming the raw acoustic signal (1202);

The signal may be adjusted for background noise. For example an empty cell may be used to capture background frequencies that may be compensated by addition or deletion in the captured acoustic signal. The background noise may be compensated for frequencies below 20 KHz and may not be compensated for frequencies above 20 KHz.

(3) Regressing and identifying relevant frequencies (1203);

(4) Generating a model for the texture attributes (1204).

This general method summary may be augmented by the various elements described herein to produce a wide variety of invention embodiments consistent with this overall design description.

It should be noted that the method used to generate the aforementioned texture attribute model may be used to generate models for other food properties such a moisture, solids content, oil content, slice thickness, density, blister density and topical seasonings. Any particles in the seasonings with a particle size of 100 microns to 500 microns may be measured with a model using the non-destructive photo acoustic method. A concentration by weight of the seasonings may be calculated from the particle size. For example, a concentration of a seasoning such as sodium chloride may be measured with a model developed with the photo acoustic method as aforementioned in FIG. 12. The relevant frequencies and associated intensities and the coefficients of the developed model may change depending on the food property that is measured with the photo acoustic method.

Exemplary Acoustic Photo Acoustic Signal Generation Method (1300)

As generally shown in FIG. 13, an exemplary Photo Acoustic Signal Generation method may be generally described in terms of the following steps:

(1) Creating small region of highly-heated material in a food snack (1301);

(2) Expanding the material rapidly (1302);

(3) Creating pressure waves from the material (1303);

(4) Propagating the pressure waves through the air as sound (1304).

This general method summary may be augmented by the various elements described herein to produce a wide variety of invention embodiments consistent with this overall design description.

The acoustic model may be developed using the method described in FIG. 9 (0900). The model may be programmed into the tool (1306) for measuring one or more texture attributes such as hardness, fracturability and denseness. An acoustic model for texture attribute hardness may be described below:

$$\text{Hardness}=f(X_{1\text{-}n}, I_{1\text{-}n})$$

$$\text{Hardness}=I_1C_1+I_2C_2+I_3C_3+\ldots+I_nC_n \quad (1)$$

Where, $I_n$ is an intensity associated with a frequency $X_n$ $C_n$ is a coefficient associated with the frequency $X_n$ Coefficients ($C_1$-Cn) are determined using the energy excitation method described in FIG. 9 (0900). A signal processing unit in the texture measurement tool (1306) identifies the relevant frequencies ($X_n$) and associated intensities ($I_n$). The tool (1306) may calculate a texture attribute such as hardness from the above model 1 by substituting the coefficients values ($C_1$-Cn) from a stored table for the food snack and the intensities ($I_n$) from the processed acoustic signal. Similarly, other texture attribute such as fracturability and denseness may be calculated from their respective models comprising the respective coefficients. It should be noted that even though the above represented model (1) shows a linear relationship between the texture attribute and intensities, a quadratic or polynomial model may also be represented to calculate the texture attributes. The hardness may also be compensated for changes in temperature of the food snack and the distance of the food snack from the focal point of the laser beam.

Similar acoustic models may be developed for models for other food properties such a moisture, solids content, oil content, slice thickness, density, blister density and topical seasonings. The relevant frequencies and associated intensities and the coefficients of the developed model may change depending on the food property. A generic model that may represent a food property of a food snack or a liquid may be described below:

$$\text{Food property}=f(Z_{1\text{-}n}, P_{1\text{-}n})$$

$$\text{Food Property}=P_1D_1+P_2D_2+P_3D_3+\ldots P_nD_n \quad (2)$$

Where, $I_n$ is an intensity associated with a frequency $X_n$ $C_n$ is a coefficient associated with the frequency $X_n$ Coefficients ($D_1$-$D_n$) are determined using the energy excitation method described in FIG. 9 (0900). A signal processing unit in the texture measurement tool (1306) identifies the relevant frequencies ($Z_n$) and associated intensities ($P_n$). In addition to texture attribute, the tool (1306) may calculate a food property from the above model (2) by substituting the coefficients values ($D_1$-Dn) from a stored table for the food snack and the intensities ($P_n$) from the processed acoustic signal. The food properties may include Solids content, Moisture, Density, Oil content, Slice thickness, Seasoning particle size, and elements such as sodium, calcium, copper, zinc, magnesium, and potassium. For liquids the food property may include viscosity, density, mouthfeel, astringency, mouth coating, sweetness, sensory, and rheology.

It should be noted that even though the above represented model (1) shows a linear relationship between the texture attribute and intensities, a quadratic or polynomial model may also be represented to calculate the texture attributes. The food property may also be compensated for changes in temperature of the food snack and the distance of the food snack from the focal point of the laser beam. A table 1.0 may be used to measure food properties of food snacks or liquids as shown below from a captured and processed acoustic signal. The values shown below in table 1.0 are for illustration purposes only and should not be construed as a limitation.

TABLE 1.0

| Food Property | Relevant Frequencies ($Z_n$) | Intensities ($P_n$) | Coefficients ($D_n$) | Value | Limits |
|---|---|---|---|---|---|
| Texture | 14000 Hz | 68 | 3.5 | 7 | 4 to 10 |
| Attribute | 15000 Hz | 71 | 2.3 | | |
| Viscosity | 16000 Hz | 75 | 1.1 | 17 | 12 to 25 |
| | 33,000 Hz | 77 | 9.0 | | |
| Density | 88000 Hz | 83 | 8.2 | 1.3 | 1 to 12 |
| Oil content | 16000 Hz | 59 | 2.5 | 36% | 20% to 46% |
| | 49,000 Hz | 70 | 2.9 | | |
| Mouthfeel | 76000 Hz | 64 | 4.3 | 0.055 | 0.035 to 0.075 |
| Astringency | 64000 Hz | 74 | 8.8 | 0.5% | 0.1% to 15% |
| Sweetness | 97000 Hz | 82 | 3.7 | 0.12 | 0.01 to 1.0 |

In a manufacturing process, as the food snacks on a conveyor belt pass from a processing unit to a seasoning station, the excitation tool in a measurement tool placed in line may strike the food snack repeatedly for a set period of time. According to a preferred exemplary embodiment, the excitation tool may continuously strike the food snack for a period of 1 micro second. According to a yet another preferred exemplary embodiment, the excitation tool may continuously strike the food snack for a period of 1 second. According to a more preferred exemplary embodiment, the excitation tool may continuously strike the food snack for a period of 1 micro second to 10 seconds. According to a most preferred exemplary embodiment, the excitation tool may continuously strike the food snack for a period of 13 seconds. The excitation tool may strike a particular food snack on the conveyor belt repeatedly so that multiple acoustic signals are generated for the entire surface of the food snack. It is known that the texture attribute may not be uniform across the entire surface. The excitation energy may strike the food snack across the entire area of the food snack so that any imperfections such as blisters may be detected after the signal has been processed. According to a preferred exemplary embodiment, repeatable measurements for a period of time, enables the measurement tool to identify subtle variations across the entire surface of a food snack. The signal may be captured/recorded by an acoustic capturing device in the texture measurement tool.

The acoustic capturing device may capture the acoustic signal across a wide range of frequencies. Additionally, the acoustic capturing device may be placed an angle directly above the food snack. According to a preferred exemplary embodiment, the acoustic capturing device captures acoustic signals in a unidirectional manner. According to another preferred exemplary embodiment, the acoustic capturing device captures acoustic signals in an omnidirectional manner. The acoustic capturing device may forward the captured acoustic signal to a processing device physically through a cable. According to a preferred exemplary embodiment, the acoustic capturing device is a wireless microphone that contains a radio transmitter. In a preferred exemplary embodiment, the acoustic capturing device is a dynamic microphone. In another preferred exemplary embodiment, the acoustic capturing device is a fiber optic microphone. A fiber optic microphone converts acoustic waves into electrical signals by sensing changes in light intensity, instead of sensing changes in capacitance or magnetic fields as with conventional microphones. The acoustic capturing device may use electromagnetic induction (dynamic microphones), capacitance change (condenser microphones) or piezoelectricity (piezoelectric microphones) to produce an electrical signal from air pressure variations. The microphones may be connected to a preamplifier before the signal can be amplified with an audio power amplifier or recorded. The microphones may be regularly calibrated due to the sensitivity of the measurement. In another preferred exemplary embodiment, the acoustic capturing device has a digital interface that directly outputs a digital audio stream through an XLR or XLD male connector. The digital audio stream may be processed further without significant signal loss. According to a preferred exemplary embodiment the acoustic capturing device may be a hydrophone. The hydrophone may be in communication with a data processing unit. The hydrophone may be used in fluid environments.

Exemplary Acoustic Signal Processing Method (1400)

As generally shown in FIG. 14, an exemplary Photo Acoustic Signal Processing method may be generally described in terms of the following steps:

(1) Receiving a raw acoustic signal (1401);
(2) Smoothing the raw acoustic signal with a windowing function to create a smoothened acoustic signal (1402);
(3) Transforming the smoothened acoustic signal into a frequency domain signal (1403);
(4) Increasing the signal-to-noise of the frequency domain signal (1404); and
(5) Normalizing and bucketing the frequency domain signal (1405).

This general method summary may be augmented by the various elements described herein to produce a wide variety of invention embodiments consistent with this overall design description.

Exemplary Acoustic Statistical Processing Method (1500)

As generally shown in FIG. 15, an exemplary statistical processing method may be generally described in terms of the following steps:

(1) Receiving a frequency domain acoustic signal (1501);

(2) Selecting variables based on dimensionality reduction of the frequencies in the frequency domain acoustic signal (1502);
(3) Filtering selected variables with a principal component analysis (1503);
(4) Performing subset regression of the filtered variables (1504); and
(5) Generate a model of texture attributes with the filtered variables (1505).

The filtered variables may be the relevant frequencies in the acoustic signal that show a strong correlation. (Adjusted $R^2>0.9$)

This general method summary may be augmented by the various elements described herein to produce a wide variety of invention embodiments consistent with this overall design description.

Exemplary Food Snack Finger Printing Method (1600)

As generally shown in FIG. 16, an exemplary food snack finger printing method may be generally described in terms of the following steps:

(1) Striking a food snack with energy from an energy excitation tool (1601);
(2) generating an acoustic signal from the food snack (1602);
(3) capturing the acoustic signal with an acoustic capturing device (1603);
(4) forwarding the acoustic signal to a data matching unit (1604);
(5) measuring a food property number of the food snack with a photo acoustic model (1605);
(6) comparing the food property number with an entry in a matching table (1606);
(7) if a match exists in step (1606), finger printing the food snack (1607); and
(8) if a match does not exist in step (1606), adding the food snack to the database for further use (1608).

This general method summary may be augmented by the various elements described herein to produce a wide variety of invention embodiments consistent with this overall design description.

Exemplary Food Property Matching Table (1700)

As generally illustrated in FIG. 17, an exemplary food property matching table (1700) is shown. The table may include a food snack in column (1701) and an associated food property (1702) in another column. The entries (1711, 1712) may include data for the food snack and food property respectively and the entries may be used for matching purposes. For example, food snack column (1701) may comprise various solids and their associated texture in column (1702). Each of the entries in the table (1700) may be populated after a photo acoustic model for the food snack has been developed by the aforementioned methods described in FIG. 12 (1200). For example, an entry (1711), may be a potato chip A. A range for the texture or other food properties may be determined with the photo acoustic model for the potato chip A and entered as an entry in table (1700). Similarly, food properties for other food products are measured with the photo acoustic model and entered into the table. The photo acoustic model may or may not be correlated with an expert panel number. The food property number may be a single texture attribute, a combination of texture attributes or a composite number comprising a combination of other food properties such as moisture, oil content, slice thickness, brittleness, solids content and so on when a food snack is measured with a photo acoustic measurement method a food property number may be determined. The food property number may be obtained from a single sample or an average of multiple samples. The measured food property number may then be looked up in the column (1702) in the matching table (1700) and a corresponding food snack is determined in the column (1701). Thereby, a food snack is finger printed based on photo acoustic measurement. According to an exemplary embodiment, food snacks with subtle differences in food property may be differentiated with the food finger printing technique. For examples, various potato chips such as baked, fried, and/or textured may be differentiated by measuring each of them and looking up the corresponding potato chip in the matching table (1700) from the measured food property numbers. Foods may be separated into buckets with the photo acoustic measurement and matching process as aforementioned in FIG. 16 (1600).

Exemplary Acoustic Signal Time Domain to Frequency Domain Conversion (1800)

As generally illustrated in FIG. 18, an exemplary acoustic signal captured in time domain (transient) (1810) is converted to a frequency domain (1820) with Fourier transformation. When an electromagnetic wave such as a laser strikes a food snack, an acoustic signal is captured in time domain and is recorded and plotted as Intensity (dB) vs. Time (secs). The recorded acoustic signal may be transformed into a frequency domain signal as illustrated in FIG. 18 (1820). The transformed acoustic signal may be further processed to identify relevant frequencies based on a statistical regression analysis. An acoustic model to quantitatively measure a texture attribute may be developed with the identified relevant frequencies and their associated intensities as variables.

Exemplary Texture Attribute vs. Relevant Frequencies Chart (1900-2100)

As generally illustrated in FIG. 19 and FIG. 20, an exemplary texture attribute Intensity vs. relevant frequencies chart may be used to compute the texture attribute of a food snack. The relevant frequencies may be identified by a statistical regression for a particular texture attribute and a food snack. For example, frequencies (1901) may be relevant for hardness and frequencies (2001) may be relevant for fracturability as determined by a statistical analysis described in FIG. 9 (0900). According to a preferred exemplary embodiment, the relevant frequencies and corresponding intensities identified in a transformed acoustic signal may be substituted in an acoustic model to quantitatively measure a texture attribute such as hardness. It should be noted that the frequencies indicated on x-axis are frequency "buckets" as determined by an algorithm, and not the literal frequencies (i.e. 400 may not be 400 Hz, but more like 18,000 Hz).

As generally illustrated in FIG. 21, an exemplary texture attribute Intensity (dB) (2101) vs. relevant frequencies (2102) chart for a food snack treated with various input conditions. Plot (2114), (2115), (2116) are frequency vs Intensity graphs for a potato chip with different solid content, moisture content and hardness of the input ingredients such as potatoes. For example, a plot (2114) may be a frequency vs intensity plot for a food snack that has a different solids content in the input ingredients. Similarly, a plot (2115) may be a frequency vs intensity plot for a food snack that has a different moisture content and different hardness in the input ingredients respectively. A plot (2106) may be plotted for background noise so that the resulting plot may be compensated for the noise. After identifying the relevant frequencies for a food snack such as a potato chip, an acoustic signal may be captured for each of the input conditions and the acoustic signal may be further processed to determine the intensities associated with the identified frequencies for the food property of the food snack. For example in FIG. 21, an identified frequency 40000 Hz may have an intensity of 75 dB (2103) for plot (2113), an intensity of 74 dB (2104) for plot (2114) and an intensity of 76 dB (2105) for plot (2115). The intensities may be substituted into a food property model generated by aforementioned equation (2) and a food property such as a texture attribute may be calculated. As illustrated in FIG. 21, the 3 different input conditions of the food ingredients (solids content, moisture content and hardness) resulted in 3 different associated intensities which further result in 3 different texture attributes. Therefore, an acoustic signal may be captured and processed for a food product and a texture attribute may be calculated based on the relevant frequencies. The input conditions may be tailored to achieve a desirable texture attribute value that is within a predefined limit. The predefined limit may be correlated to a qualitative descriptive panel number. Similarly, plots may be generated for various food properties by capturing an acoustic signal and processing it. The intensities associated with the various food properties at their respective frequencies may be determined and the food property may be calculated. A model may be generated for each of the food properties through signal processing and statistical regression as aforementioned. Therefore, a photo acoustic method may be used to identify differences in a food product based on any food property such as a texture attribute, solids content, moisture, oil content, density, blister density and elements such as Sodium, Potassium, Calcium, and Magnesium. The differences in the food product may be as minor as +−5% of the desirable value. For example, a desirable hardness value of 75 may be differentiated from a hardness value of 70 that may be undesirable for the food product. The food product with the undesirable value (70) may be rejected and not further processed or packaged.

Exemplary Embodiment Liquid Texture Measurement Tool (2200)

The present invention may be seen in more detail as generally illustrated in FIG. 22, wherein an exemplary liquid texture measurement tool (2200) comprises a housing, an energy excitation tool (2201) such as a laser generator that may be attached to the housing and positioned to direct electromagnetic wave ("energy") such as a laser (2207) towards a liquid (2209) placed in a container (2219) on a food staging station (2205). The laser generator may be independently positioned without attaching to the housing. The physical and chemical interaction of a liquid in the mouth include steps from initial perception on the palate to the act of swallowing. According to an exemplary embodiment, the perception on the palate and the mouthfeel is quantitatively modeled with a photo acoustic method as described in FIG. 23 and a correlation method as described in FIG. 24. The liquid may be a carbonated cold beverage, non-carbonated cold beverage, wine, or hot liquids such as coffee or soup. According to a preferred exemplary embodiment, the liquid is a carbonated beverage. In some instances, the carbonated beverages may be de-gassed by sonication wherein bottles with the carbonated beverages may be lightly tapped into a sonication bath until the gas is substantially released from solution. This process may be repeated until a sufficient amount of gas is removed from the fluid to allow the bottles to be placed in the bath without risk of overflow. The beverages may be left in the sonication bath for a period of time, for example between 1 minute and 5 hours. Example of the beverage may be one of Regular Pepsi (High Fructose Corn Syrup), Diet Pepsi, Sugar Cane Mountain Dew, Sugar Cane Pepsi, Gatorade, or Deionized Water. It should be noted that sonication may be used to decouple the effect of bubbles in the beverage when an acoustic signal is generated by laser excitation. In some instances, the carbonated beverage may not be de-gassed and an acoustic signal may be generated by laser excitation with the bubbles in the carbonated beverage. The effect of bubbles in the beverage may be further compensated by statistical models. After sonication, the liquids/beverages may be left open to equilibrate. A portion if the sonicated liquid for example, 100 mL, may be contained in an individual beaker. In some embodiments, the amount of liquid may range from 1 mL to 1 Liter. The beaker is typically a cylindrical shaped and configured to hold the liquid. It should be noted that the shape of the beaker could be selected such that liquid contained in the beaker provides sufficient exposure of surface area to a laser beam. Each beaker with the individual liquid may be placed in a lasing chamber or exposed to a laser, where a laser beam typically with an energy 24 mJ and spot size 300 microns may be directed at a single spot, resulting in an acoustic response. In some embodiments the laser energy may range from 1 mJ to 100 mJ. In more preferred embodiments the laser energy may range from 10 mJ to 50 mJ. In most preferred embodiments the laser energy ranges from 20 mJ to 30 mJ. The spot size of the laser may range from 1 micron to 1000 microns. In some preferred embodiments, the spot size of the laser may range from 10 micron to 400 microns. In most preferred embodiments, the spot size of the laser may range from 100 micron to 500 microns. Each liquid may be individually tested, with at least 2 replicates completed for each cell. According to another preferred exemplary embodiment, the liquid is a non-carbonated beverage. The food staging station may be a stationary surface. According to a preferred exemplary embodiment, the energy excitation tool is a laser generating unit that generates lasers. The staging station (2205) may be a flat surface that is used for developing an acoustic model. In other embodiments, the liquid may be moving in a pipe in a manufacturing process on-line. According to an exemplary embodiment, an acoustic capturing device (2203) may be positioned to record/capture an acoustic signal (2206) from the liquid (2209). The acoustic capturing device (2203) may be in communication with a data processing unit (DPU) (2204) via a cable (2202) or wirelessly. The acoustic capturing device may capture the acoustic signal across a wide range of frequencies 0 Khz to 5000 KHz. In a preferred embodiment, the acoustic capturing device may capture the acoustic signal across a range of frequencies 0 KHz to 100 KHz. In another preferred embodiment, the acoustic capturing device may capture the acoustic signal across a range of frequencies 200 KHz to 400 KHz. The acoustic capturing device may be a contact transducer that may be coupled to the container directly. The transducer may measure a longitudinal component of the acoustic signal. The longitudinal component may be a component through the liquid. Additionally, a transverse or shear component (distance between peaks of the signal) of the acoustic signal may be captured with a surface acoustic wave sensor. The acoustic signal may be a combination of the transverse and longitudinal components. Alternatively, the acoustic capturing device may be a microphone that may capture acoustic signal through the air. Additionally, the acoustic capturing device (2203) may be placed at an angle directly above the liquid (2209). According to a preferred exemplary embodiment, the acoustic capturing device captures acoustic signals in a unidirectional manner. The acoustic capturing device may be in communication with a data processing unit. In another preferred exemplary embodiment, the acoustic capturing device is a fiber optic microphone. The acoustic capturing device (2203) may be placed at a pre-determined distance and a pre-determined angle from the liquid (2209). The pre-determined distance may be chosen such that it produces maximum energy density from the liquid. The distance (2208) from the bottom of energy excitation tool (2201) to the top of the container (2219) is selected so that the energy beam (laser) is safe within the manufacturing environment. Differing levels of carbonation may be compensated by generating acoustic responses from de-carbonated beverage substrates. However, acoustic responses from carbonated liquids may be generated to correlate a true taste of the carbonated liquid with a photo acoustic response. While it is apparent that perception is possible based on density related to calories and/or solids, it is also noted that each of these beverages exhibits quantifiable textural, sensory, and rheological properties as well.

According to a preferred exemplary embodiment, fluence (energy per unit area) at the liquid surface is between 15 mJ/mm2 and 700 mJ/mm2. According to a more preferred exemplary embodiment, fluence at the liquid surface is between 1 mJ/$cm^2$ and 700 mJ/$mm^2$. According to a yet another preferred exemplary embodiment, fluence at the liquid surface is between 1 mJ/$cm^2$ and 350 mJ/$mm^2$. The fluence could be varied by changing the energy of the laser or the spot size (area) of the laser.

In one embodiment, the acoustic response may be a vibration of the bottom of the beaker containing the liquid which may be observed by a plasma arc present upon ablation of the test sample. The vibration of the beaker, and subsequent attenuation and dampening of the acoustic signal of the beaker resulting from the rheological properties of the liquid like viscosity, surface tension, or density may be some of the primary signals captured in the acoustic response. The size, dimensions, and material of the beaker may be some of the factors affecting the vibration of the beaker and/or dampening of the acoustic response. These factors may be compensated by additional statistical modeling and added coefficients. The optimal fluid container/beaker for photoacoustic beverage testing may be determined by the type of the liquid. The height of liquid column may effect part of the acoustic response as a result of greater beam attenuation and energy losses through the liquid. In some instances, optical properties of the liquid, may partially drive acoustic response. Other factors such as the shape of the beaker ("container"), diameter of the beaker, material of the beaker, thickness of the beaker walls and beaker bottom may further effect the acoustic response when a laser strikes the liquid in the beaker. Additionally, use of an accelerometer, or similar contact-driven pressure transducer, may improve signal fidelity and thus, final separation of liquid types.

The acoustic capturing device (2203) may be connected physically with a conducting cable to the DPU (2204) via an input-output module in the DPU (2204). The energy excitation tool (2201) is positioned to direct energy towards a food snack (2209). It should be noted that the angle of directing as shown is for illustration purposes only. The angle of directing the energy may be configured to produce an optimal excitation of the food snack such that an acoustic capture device (2203) may capture a complete acoustic signal after the excitation tool directs energy towards the food snack. The acoustic signal may then be captured for a period of time. The acoustic signal may be represented as Intensity (dB) vs. Time (secs). According to a preferred exemplary embodiment, the acoustic signal is captured for 1 sec to 5 minutes. According to yet another preferred exemplary embodiment, the acoustic signal from the food snack is captured for 2 sec. According to a more preferred exemplary embodiment, the acoustic signal from the food snack is captured for 1 sec. According to a most preferred exemplary embodiment, the acoustic signal from the food snack is captured for 10 sec.

According to a preferred exemplary embodiment, the energy excitation tool directs energy towards the food snack for a pulse duration or firing time of 5 nanoseconds to 5 minutes. According to yet another preferred exemplary embodiment, the energy excitation tool directs energy towards the food snack for 1 nanosecond. According to a more preferred exemplary embodiment, the energy excitation tool directs energy towards the food snack for 1 minute. According to a most preferred exemplary embodiment, the energy excitation tool directs energy towards the food snack for 9-12 nanoseconds.

According to a preferred exemplary embodiment, a quantitative photo acoustic model enables to compensate for the effect of saliva on the mouthfeel and the interaction in a mouth. By leveraging photo acoustic correlation methods, when a beverage item is consumed additional information on texture information may be captured with the acoustic fingerprint of each beverage item include the interaction with saliva. For example, to distinguish the viscosity of a Diet Pepsi® vs. a regular Pepsi® is difficult given the measurement error with methods currently available. When in contact with saliva, different sweeteners can have different interactions with human saliva given their chemical composition, the mixture of the beverage and the saliva produces viscosity differences that can be differentiated by a photo acoustic model (2300) and texture correlation method as described in more detail in FIG. 24 (2400). The photo acoustic quantitative correlation method with qualitative means enables rapid, on-line quantification of liquid textures and other physical properties which further may enable raw material selection/evaluation, exploration of alternative sweetening systems, rapid product design, design execution, quality management, and real time process control and automation.

As generally shown in FIG. 23 (2300), an exemplary texture measurement method may be generally described in terms of the following steps:

(1) striking a surface of a liquid with a laser, thereby generating an acoustic signal from the surface of the liquid (2301);

(2) capturing the acoustic signal with an acoustic capturing device (2302);

(3) sending the acoustic signal to a data processing unit coupled to the acoustic capturing device (2303);

(4) converting the acoustic signal from a time domain to a frequency domain (2304);

acoustic signal is generally captured for a period of time and the signal is plotted as Intensity (dB) vs. Time (seconds)

(5) identifying relevant frequencies and their associated intensities (2305); and (6) quantifying the texture attribute of the liquid based on said relevant frequencies and said associated intensities (2306).

The texture attribute may be viscosity, density, mouthfeel, astringency, mouth coating, sweetness, sensory, and rheology.

This general method summary may be augmented by the various elements described herein to produce a wide variety of invention embodiments consistent with this overall design description.

As generally shown in FIG. 24 (2400), an exemplary liquid texture correlation method may be generally described in terms of the following steps (1) Providing liquid samples to an expert panel (2401);

(2) Qualitatively analyzing the liquid samples (2402);

Qualitatively measure texture attributes by the expert panel through mouthfeel or chewing or swallowing or other drinking means for assigning taste scores ("descriptive panel number").

(3) Assigning a descriptive panel number for the texture attributes of the liquid sample (2403);

A descriptive panel number ("taste score") could be assigned to each of the texture attributes such as viscosity, density, mouthfeel, astringency, mouth coating, sweetness, sensory, and rheology.

(4) Measuring texture attributes using a non-invasive photo acoustic analytical method (2404);

As described in FIG. 23, acoustic responses may be generated from the liquid samples by laser excitation followed by identifying relevant frequencies and associated intensities.

(5) Correlating the analytical and the qualitative texture attributes (2405); and A photo acoustic texture model used to measure a texture attribute may be compensated or adjusted for changes in the properties of the human saliva such as viscosity and pH. The photo acoustic model may be compensated with different coefficients to account for individual human saliva and chewing preferences. For example, Human A may be chewing with saliva having a viscosity A and pH A and use a chew pattern A. Human B may be chewing with saliva having a viscosity B and pH B and use a chew pattern B. When the photo acoustic model is developed using method described in FIG. 23 (2300), the coefficients may be different for Human A vs. Human B to account for the differences. A unique model may be used for each of the texture attributes. Therefore, the texture attribute would be same independent of the human eating/drinking the solid/liquid. Coefficients for the model may be statistically adjusted or compensated for saliva properties and chewing mechanism for each of the texture attributes and adjusted for each of the human beings in the expert panel.

(6) Generating a correlation model for the texture attributes (2406).

The adjusted $R^2$ of the correlation may be targeted to be greater than 0.7. In more preferred exemplary embodiments, the adjusted $R^2$ of the correlation may be greater than 0.7. In most preferred exemplary embodiments, the adjusted $R^2$ of the correlation may be greater than 0.9.

A beverage or a liquid for consumer consumption may depend on several factors such as mouthfeel, sweetness, astringency, mouth coating, sweetness, sensory, and rheology. Some additives or modifiers may be used to target a specific attribute that a consumer may like while keeping the other factors constant. For example a mouth feel of beverage A vs. beverage B may be different, but a consumer may like one or the other depending on the sweetness. If the sweetness of beverage A is liked by consumer, then beverage B can be targeted to the same sweetness of beverage A by adding modifiers such as mouthfeel modifiers, sweeteners, starch, gums, enzymes, emulsions, pH modifiers and the like. An exemplary formulation may be generally shown in FIG. 25 (2500), an exemplary quantitative method for formulating a liquid to target a texture attribute of consumers, the method may be generally described in terms of the following steps:

1) conducting a tasting test with at least one consumer with a plurality of liquids (2501);

For example, two consumers (consumer A and Consumer B) may be selected for the test to taste two beverages (beverage A and beverage B).

2) identifying a qualitative measure of the texture attribute or liquid attribute for each consumer and each of the plurality of liquids (2502);

an attribute such as sweetness and mouthfeel may be selected as the attributes to measure.

3) assigning a texture score ("taste score") for each of the plurality of liquids (2503);

consumer A and Consumer B may assign taste scores for sweetness and mouthfeel for beverage A and beverage B.

4) characterizing each of the plurality of liquids with a photo acoustic method (2504);

beverage A and beverage B may be characterized with a photo acoustic method described in the method in FIG. 23.

5) identifying relevant frequencies and their associated intensities for each of the plurality of liquids (2505);

The relevant frequencies and their associated intensities may be identified with the photo acoustic method and statistical methods as aforementioned.

6) correlating the texture score with the relevant frequencies (2506); and

The texture score in step (3) may be correlated with the identified frequencies for each of the liquids/beverages and statistically adjusted for the differences in the consumers.

7) targeting a formulation based on the relevant frequencies and associated intensities (2507).

If a particular attribute, for example sweetness of beverage A is likable to both consumers, then beverage B can be formulated to the same sweetness of beverage A by adding modifiers such as mouthfeel modifiers, sweeteners, starch, gums, enzymes, emulsions, pH modifiers and the like. Acoustic responses after laser excitation may be recorded for each of the modifications for beverage B. The identified frequencies and associated intensities for each of modified formulations for beverage B may then be evaluated against the frequencies and associated intensities for beverage A. The closest matched frequencies and associated intensities after statistical adjustments may be the formulation of beverage B that may provide the same sweetness of beverage A while keeping the other attributes substantially the same. Similarly, other attributes may be targeted for a formulation. Additionally a reference standard such as a deionized water may be used to provide a baseline for the targeted formulation. A beverage which is acidic may generate an acoustic signal associated with frequencies and intensities that are different than a non-acidic beverage. The different signatures or frequencies in the acidic and non-acidic beverage may enable to differentiate the beverages. Similarly, a coffee with a flavor A when excited with a laser may generate an acoustic signal A associated with frequencies A. Similarly, a coffee with a flavor B when excited with a laser may generate an acoustic signal B associated with frequencies B. Based on an acoustic response from an unidentified coffee and a taste score from a taste testing of known and characterized coffee, a flavor for the unidentified coffee may be targeted. The coffee beans may be modified to generate a flavor and when excited with a laser generate an acoustic signal that matches with aforementioned frequency A or frequency B. Similarly, a coffee A and coffee B may be differentiated and identified or separated based on the acoustic signal generated and frequencies identified. It may be noted that a database may be maintained with liquid types and their associated frequencies. When an unknown liquid is excited with a laser and an acoustic signal is generated, the unknown liquid may be identified based on the acoustic signal. The method may be implemented for wine tasting, beverage tasting, or when targeting a formulation for a beverage.

The exemplary method described above enables to measure the balance and other components in a wine without the need for extensive wine tasting. The exemplary methods in FIG. 23-25 may be utilized to measure a balanced wine for its basic flavor components in good proportion along with interaction with the taste buds that detect sweet, sour, salty, and bitter. Some of the attributes of a wine such as Sweet (residual sugar) and sour (acidity) are can be modelled with a photo acoustic method. Similarly, the exemplary quantitative photo acoustic method enables to measure coffee flavors and taste without the need for coffee tasting.

This general method summary may be augmented by the various elements described herein to produce a wide variety of invention embodiments consistent with this overall design description.

FIG. 26 is an exemplary statistical chart illustrating separation of liquids based on a quantitative texture attribute according to a preferred embodiment of the present invention. The results of the various liquids derived with photo acoustic models may differentiate beverages with similar textural/mouth feel properties as illustrated in FIG. 26. The data represents analysis using statistical software and PLS with solid as measured by total calorie content, sodium content, and sugar content as a response. Data show strong separation of beverage classes, especially as driven by total solids content. Textural attributes (mouthfeel) may be correlated with rheological and visco-elastic properties of the liquids.

System Summary

The present invention system anticipates a wide variety of variations in the basic theme of texture measurement apparatus that includes an energy excitation tool, an acoustic capturing device, and a data processing unit. The energy excitation tool directs a laser towards a liquid in a container and creates pressure waves that propagate through the air and produce an acoustic signal. The acoustic capturing device records and forwards the signal to a data processing unit. The data processing unit further comprises a digital signal processing module that smoothens, transforms and filters the received acoustic signal. A statistical processing module further filters the acoustic signal from the data processing unit and generates a quantitative acoustic model for texture attributes such as mouthfeel and rheological properties. The quantitative model is correlated with a qualitative texture measurement from a descriptive expert panel. Texture of liquids are quantitatively measured with the quantitative acoustic model.

This general system summary may be augmented by the various elements described herein to produce a wide variety of invention embodiments consistent with this overall design description.

Method Summary

The present invention method anticipates a wide variety of variations in the basic theme of implementation, but can be generalized as a quantitative method for measuring texture attribute of a food snack, the method comprises the steps of:

a) striking a surface of a liquid with a laser, thereby generating an acoustic signal from the liquid;
b) capturing the acoustic signal with an acoustic capturing device;
c) sending the acoustic signal to a data processing unit coupled to the acoustic capturing device;
d) converting the acoustic signal from a time domain to a frequency domain;
e) identifying relevant frequencies and their associated intensities; and
f) quantifying the texture attribute of the liquid based on the relevant frequencies and the associated intensities.

This general method summary may be augmented by the various elements described herein to produce a wide variety of invention embodiments consistent with this overall design description.

System/Method Variations

The present invention anticipates a wide variety of variations in the basic theme of a quantitative texture measurement. The examples presented previously do not represent the entire scope of possible usages. They are meant to cite a few of the almost limitless possibilities.

This basic system and method may be augmented with a variety of ancillary embodiments, including but not limited to:

- An embodiment wherein the liquid is contained in an open container when the laser strikes the liquid.
- An embodiment wherein the liquid is passing within a tube when the laser strikes the liquid.
- An embodiment wherein the acoustic capturing device is configured to capture frequencies in the acoustic signal; the frequencies range from 0 to 5000 KHz.
- An embodiment wherein a distance between the acoustic capturing device and the product ranges from 2 inch to 2 feet.
- An embodiment wherein the laser generator is configured to generate the laser that imparts fluence within a range of 1 $mJ/cm^2$ to 700 $mJ/mm^2$.
- An embodiment wherein the liquid is a carbonated beverage.
- An embodiment wherein the liquid is a non-carbonated beverage.
- An embodiment wherein the data processing unit further comprises a digital signal processing unit and a texture attribute computing unit.
- An embodiment wherein the digital signal processing unit is configured to smoothen, transform and filter the acoustic signal to identify relevant frequencies relating to the texture attribute.

An embodiment wherein the texture attribute computing unit is configured to determine the texture attribute from the frequencies captured in the acoustic signal.

An embodiment wherein the texture attribute is selected from a group comprising: viscosity, density, mouthfeel, astringency, mouth coating, sweetness, sensory, and rheology.

An embodiment wherein when the laser strikes a surface of the liquid, the laser creates an arc in the bottom of the container.

An embodiment wherein the acoustic capturing device is a microphone; the microphone is configured to be wired to the data processing unit.

An embodiment wherein the acoustic capturing device is a microphone; the microphone is configured to wirelessly connect with the data processing unit.

One skilled in the art will recognize that other embodiments are possible based on combinations of elements taught within the above invention description.

What is claimed is:

1. A photo acoustic quantitative method for measuring a texture attribute of a liquid, the method comprising the steps:

a) striking a surface of the liquid with a laser and creating an arc, thereby generating an acoustic signal from the struck surface of the liquid;

b) capturing the acoustic signal with an acoustic capturing device positioned above the struck surface of the liquid;

c) sending the acoustic signal to a data processing unit coupled to the acoustic capturing device;

d) converting the acoustic signal from a time domain to a frequency domain;

e) identifying (1) relevant frequencies of the converted acoustic signal and (2) associated intensities for the relevant frequencies; and f) quantifying the texture attribute of the liquid based on the relevant frequencies and the associated intensities.

2. The method of claim 1, wherein the liquid is contained in an open container when the laser strikes the liquid.

3. The method of claim 1, wherein the liquid is passing within a tube when the laser strikes the liquid.

4. The method of claim 1, wherein the laser strikes the liquid at multiple locations of the liquid.

5. The method of claim 1, wherein the acoustic capturing device captures the acoustic signal for a period of 1 second to 5 minutes.

6. The method of claim 1, wherein the laser strikes the liquid continuously for a period of 1 micro second to 10 seconds.

7. The method of claim 1, wherein the liquid is elected from a group consisting of: carbonated beverage, non-carbonated beverage, hot liquids, wine, coffee, and cold beverages.

8. The method of claim 1, wherein the texture attribute is selected from a group comprising: viscosity, density, mouthfeel, astringency, mouth coating, sweetness, a sensory property, and a rheological property.

* * * * *